(12) United States Patent
Kaur et al.

(10) Patent No.: US 12,226,462 B2
(45) Date of Patent: Feb. 18, 2025

(54) FIBRINOLYTIC COMPOSITION AND METHOD OF ITS PREPARATION

(71) Applicant: Council of Scientific and Industrial Research, New Delhi (IN)

(72) Inventors: Navneet Kaur, Chandigarh (IN); Prakash Kumar, Chandigarh (IN); Girish Sahni, Chandigarh (IN)

(73) Assignee: Council of Scientific & Industrial Research, New Delhi (IN)

( * ) Notice: Subject to any disclaimer, the term of this patent is extended or adjusted under 35 U.S.C. 154(b) by 619 days.

(21) Appl. No.: 17/425,619

(22) PCT Filed: Jan. 23, 2020

(86) PCT No.: PCT/IN2020/050074
§ 371 (c)(1),
(2) Date: Jul. 23, 2021

(87) PCT Pub. No.: WO2020/152713
PCT Pub. Date: Jul. 30, 2020

(65) Prior Publication Data
US 2022/0096608 A1    Mar. 31, 2022

(30) Foreign Application Priority Data
Jan. 25, 2019  (IN) .............. 201911003104

(51) Int. Cl.
*A61K 38/48*       (2006.01)
*C12N 9/68*        (2006.01)
(52) U.S. Cl.
CPC .......... *A61K 38/484* (2013.01); *C12N 9/6435* (2013.01); *C12Y 304/21007* (2013.01)
(58) Field of Classification Search
CPC .................................................. A61K 38/484
See application file for complete search history.

(56) References Cited

U.S. PATENT DOCUMENTS 3,950,513 A    4/1976  Jensen
8,101,394 B2   1/2012  Novokhatny
9,121,014 B2   9/2015  Zwaal

FOREIGN PATENT DOCUMENTS

EP     3124496 B1    10/2018
WO     199315189 A1   8/1993
WO     2004045558 A2  6/2004

OTHER PUBLICATIONS

UniProt A0A2J8JZZ2—Published Mar. 28, 2018. Retrieved from < https://www.uniprot.org/uniprotkb/A0A2J8JZZ2/entry > on Jun. 10, 2024.*

International Search Report mailed Mar. 20, 2020 in reference to co-pending Indian Patent Application No. PCT/IN2020/050074 filed Jan. 23, 2020.
Written Opinion mailed Mar. 20, 2020 in reference to co-pending Indian Patent Application No. PCT/IN2020/050074 filed Jan. 23, 2020.
Adivitiya, et al., "The evolution of recombinant thrombolytics: Current status and future directions", Bioengineered, vol. 8, No. 4, pp. 331-358, 2017.
Ambrus, et al., "Clinical and Experimental Studies on Fibrinolytic Enzymes", pp. 1-41, 1957.
Aoki, "Discovery of $x_2$-plasmin inhibitor and its congenital deficiency", Journal of Thrombosis and Haemostasis, vol. 3, pp. 623-631, 2004.
Bailon, et al., "Polyethlene glycol-conjugated pharmaceutical proteins", Research Focus PSTT, vol. 1, No. 8, pp. 1-5, Nov. 1998.
Cazalis, et al., "C-Terminal Site-Specific PEGylation of a Truncated Thrombomodulin Mutant with Retention of Full Bioactivity", Bioconjugate Chem., vol. 15, pp. 1005-1009, 2004.
Chapman, "PEGylated antibodies and antibody fragments for improved therapy: a review", Advanced Drug Delivery Reviews, vol. 54, pp. 531-545, 2002.
Chapman, et al., "Therapeutic antibody fragments with prolonged in vivo half-lives", Nature Biotechnology, vol. 17, pp. 780-784, Aug. 1999.
Chen, et al., "Enzymatic vitreolysis with recombinant microplasminogen and tissue plasminogen activator", NPG Eye, vol. 22, pp. 300-307, 2008.
Chiu, et al., "Effects of Polymer Molecular Weight on the Size, Activity, and Stability of PEG-Functionalized Trypsin", Biomacromolecules, vol. 11, pp. 3688-3692, 2010.
Cliffton, "The Use of Plasmin in Humans", pp. 209-229, 1957 ??????
Collen, et al., "Basic and Clinical Aspects of Fibrinolysis and Thrombolysis", Blood Journal, vol. 78, No. 12, pp. 3114-*3124, Dec. 15, 1991.
Collen, "The main components of the fibrinolytic system: Biochemical and physiological properties", European Heart Journal, vol. 6, Supplement E, pp. 193-195, 1985.
Collen, et al., "Polyethylene Glycol-Derivatized Cysteine-Substitution Variants of Recombinant Staphylokinase for Single-Bolus Treatment of Acute Myocardial Infarction", Circulation, vol. 102, pp. 1766-1772, Oct. 10, 2000.
Crumrine, et al., "Safety evaluation of a recombinant plasmin derivative lacking kringles 2-5 and rt-PA in a rat model of transient ischemic stroke", Experimental & Translational Stroke Medicine, vol. 4, No. 10, pp. 1-16, 2012.
De Semet, et al., "Microplasmin: Ex Vivo Characterization of Its Activity in Porcine Vitreous", Arvo Journals, vol. 50, No. 2, pp. 814-819, Feb. 2009.
Doherty, et al., "Site-Specific PEGylation of Engineered Cysteine Analogs of Recombinant Human Granulocyte-Macrophage Colony-Stimulating Factor", Bioconjug Chem., vol. 16, No. 5, pp. 1291-1298, 2005.

(Continued)

Primary Examiner — Suzanne M Noakes
(74) Attorney, Agent, or Firm — Dinsmore & Shohl LLP

(57) ABSTRACT

The present invention discloses modified forms of plasmin with advantageous properties. As compared to their natural unmodified form, these variants exhibit significantly modulated kinetics in terms of delayed inhibition characteristics in the presence of specific inhibitors, such as $\alpha_2$-antiplasmin ($\alpha_2$-AP). These include PEG-conjugated thiol derivatives of truncated plasmin with potential clinical applications in various regimens of thrombolytic therapies.

12 Claims, 9 Drawing Sheets
Specification includes a Sequence Listing.

(56) References Cited

OTHER PUBLICATIONS

Fishburn, "The Pharmacology of PEGylation: Balancing PD with PK to Generate Novel Therapeutics", Journal of Pharmaceutical Sciences, vol. 97, No. 10, pp. 4167-4183, Oct. 2008.
Gaberc-Porekar, et al., "Obstacles and pitfalls in the PEGylation of therapeutic proteins", Current Opinion in Drug Discovery & Development, vol. 11, No. 2, pp. 242-250, 2008.
Grace, et al., "Site of Peglyation and Polyethylene Glycol Molecule Size Attenuate Interferon-x Antiviral and Antiprliferative Activites through the JAK/STAT Signaling Pathway", The Journal of Biological Chemistry, vol. 280, No. 8, pp. 6327-6336, Feb. 25, 2005.
Greenwald, et al., "Effective drug delivery by PEGylated drug conjugates", Advanced Drug Delivery Reviews, vol. 55, pp. 217-250, 2003.
Hamed, et al., "Poly(ethylene glycol) Conjugation Stabilizes the Secondary Structure of x-Helices by Reducing peptide Solvent Accessible Surface Area", Biomacromolecules, vol. 14, pp. 4053-4060, 2013.
Hao, et al., "Effects of Site-Specific Polyethylene Glycol Modification of Recombinant Human Granulocyte Colony-Stimulating Factor on its Biologic Activites", Short Communications, Biodrugs, VOI. 20, No. 6, pp. 357-362, 2006.
Harris, et al., "Effect of Pegylation on Pharmaceuticals", Nature Communications, vol. 2, pp. 214-221, Mar. 2003.
Harris, et al., "Peptide and protein pegylation II 0 clinical evaluation", Science Direct, Advanced Drug Delivery Reviews, VOI. 55, pp. 1259-1260, 2003.
Hunt, et al., "Simplified recombinant plasmin: Production and functional comparison of a novel thrombolytic molecule with plasma-derived plasmin", Blood Coagulation, Fibrinolysis and Cellular Haemostasis, pp. 413-420, Jul. 2008.
King, et at., "Improved Tumor Targeting with Chemically Cross-Linked Recombinant Antibody Fragments", Cancer Research, vol. 54, pp. 6176-6185, Dec. 1, 1994.
Kurfürat, "Detection and Molecular Weight Determination of Polyethylene Glycol-Modified Hirudin by Staining after Sodium Dodecyl Sulfate-Polyacrylamide Gel Electrophoresis", Analytical Biochemistry, vol. 200, pp. 244-248, 1992.
Lapchak, et al., "Microplasmin: A Novel Thrombolytic That Improves Behavioral Outcome After Embolic Strokes in Rabbits", Stroke Journal of the American Heart Association, vol. 33, pp. 2279-2284, 2002.
Law, et al., "X-ray crystal structure of the bibrinolysis inhibitor $x_2$-antiplasmin", Blood Journal, The American Society of Hematology, vol. 111, No. 4, pp. 2049-2053, Feb. 15, 2008.
Marder, et al., "Plasmin Induces Local Thrombolysis without Causing Hemorrhage: A Comparison with Tissue Plasminogen Activator in the Rabbit", Thromb Haemost, vol. 86, pp. 739-745, 2001.
Marder, "Historical perspective and future direction of thrombolysis research: the re-discovery of plasmin", Journal of Thrombosis and Haemostasis, vol. 9, Suppl. No. 1, pp. 364-373, 2011.
Meng, et al., "Mechanistic Insights into the Stabilization of srcSH3 by PEGylation", Langmuir, vol. 28, pp. 16133-16140, 2012.
Milla, et al., "PEGylation of Proteins and Liposomes: a Powerful and Flexible Strategy to Improve the Drug Delivery", Current Drug Medicine, vol. 13, pp. 105-119, 2012.
Mok, et al., "Evaluation of Polyethylene Glycol Modification of First-Generation and Helper-Dependent Adenoviral Vectors to Reduce Innate Immune Responses", Molecular Therapy, vol. 11, No. 1, pp. 66-79.
Nagai, et al., "Role of Plasminogen System Components in Focal Cerebral Ischemic Infarction", Basic Science Reports, pp. 2440-2444, Mar. 7, 2015.
Nagai, et al., "Depletion of circulating $x_2$-antiplasmin by intravenous plasmin or immunoneutralization reduces focal cerebral ischemic injury in the absence of arterial recanalization", Blood Journal Organization, vol. 97, No. 10, pp. 3086-3092, May 15, 2001.

Nagai, et al., "Recombinant human microplasmin: production and potential therapeutic properties", Journal of Thrombosis and Haemostasis, vol. 1, pp. 307-313, 2003.
Novokhatny, "Structure and activity of plasmin and other direct thrombolytic agents", Thrombosis Research, vol. 122, pp. 53-58, 2008.
Ozbakir, et al., "Kinetic and Transport Effects on Enzymatic Biocatalysis Resulting from the PEGylation of Confactors", vol. 64, No. 1, pp. 12-17,Jan. 2018.
Nagai, et al., "Role of Plasminogen System Components in Focal Cerebral Ischemic Infarction", Basic Science Reports, pp. 2440-2446, May 11, 1999.
Nagai, et al., "Depletion of circulating $x_2$-antiplasmin by intravenous plasmin or immunoneutralization reduces focal cerebral ischemic injury in the absence of arterial recanalization", Blood Journal, vol. 97, No. 10, pp. 3086-3093, Mat 2001.
Nagai, et al., "Recombinant human microplasmin: production and potential therapeutic properties", Journal of Thrombosis and Haemostasis, vol. 1, pp. 307-313, Oct. 2002.
Novokhatny, "Structure and activity of plasmin and other direct thrombolytic agents", Thrombosis Research, vol. 122, pp. S3-S8, 2008.
Ozbakir, et al., "Kinetic and Transport Effects on Enzymatic Biocatalysis Resulting from the PEGylation of Cofactors", American Institute of Chemical Engineers, vol. 64, No. 1, pp. 12-17, Jan. 2018.
Pakola, et al., "Neutralization of $x_2$-Antiplasmin by Microplasmin: A Randomized, Double-Blind, Placebo-Controlled, Ascending-Dose Study in Healthy Male Volunteers", Clinical Therapeutics, vol. 31, No. 8, pp. 1688-1706, Nov. 8, 2009.
Pandey, et al., "Impact of Site-Specific PEGylayion on the Conformational Stability and Folding Rate of the Pin WW Domain Depends Strongly on PEG Oligomer Length", Bioconjugate Chemistry, vol. 24, pp. 796-802, 2013.
Petersen, et al., "Characterization of the Gene for Human Plasminogen, a Key Proenzyme in the Fibrinolytic System", The Journal of Biological Chemistry, vol. 265, No. 11, pp. 3104-3111, Apr. 5, 1990.
Mu, et al., "Molecular Insight into the Steric Shielding Effect of PEG on the Conjugated Staphylokinase: Biochemical Characterization and Molecular Dynamics Simulation", PLOS One, vol. 8, Issue 7, pp. 1-10, Jul. 2013.
Reed, et al., "Microvascular Thrombosis, Fibrinolysis, Ischemic Injury and Death after Cerebral Thromboembolism Are Affected by Level of Circulating x2-Antiplasmin", Arterioscler Throm Vasc Biol., vol. 34, No. 12, pp. 2586-2593, Dec. 2014.
Reed, et al., "Inhibition of Clot-Bound $x_2$-Antiplasmin Enhances In Vivo Thrombolysis", Circulation, vol. 82, No. 1, pp. 164-168, Jul. 1990.
Reed, "Functional Characterization of Monoclonal Antibody Inhibitors of x2-Antiplasmin that Accelerate Fibrinolysis in Different Animal Plasmas", Hybridoma, vol. 16, No. 3, pp. 281-286, 1997.
Robbins, et al., "The Peptide Chains of Human Plasmin", The Journal of Biological Chemistry, vol. 242, No. 10, pp. 233-2342, May 25, 1967.
Roberts, et al., "Chemistry for peptide and protein PEGylation", Advanced Drug Delivery Reviews, vol. 64, pp. 116-127, 2012.
Sakata, et al., "Significance of Cross-Linking of $x_2$-Plasmin Inhibitor to Fibrin in Inhibition of Fibrinolysis and Hemostasis", Journal Clin. Invest., vol. 69, pp. 536-542, Mar. 1982.
Singh, et al., "Releasing the Brakes on the Fibrinolytic System in Pulmonary Emboli: Unique Effects of Plasminogen Activation and x2-Antiplasmin Inactivation", Circulation, vol. 135, No. 11, pp. 1011-1020, Mar. 14, 2017.
Suzuki, et al., "Microplasmin Reduces Ischemic Brain Damage and Improves Neurological Function in a Rat Stroke Model Monitored With MRI", Stroke Journals, pp. 2402-2406, Aug. 2004.
Thijs, et al., "Randomized, Placebo-Controlled, Dose-Ranging Clinical Trial of Intravenous Microplasmin in Patients With Acute Ischemic Stroke", Stroke Journals, pp. 3789-3795, 2009.
Tovchigrechko, et al., "GRAMM-X public web server for protein-protein docking", Nucleic Acids Research, vol. 34, pp. W310-W314, 2006.
Turner, et al., "Structural Elements That Govern the Substrate Specificity of the Clot-dissolving Enzyme Plasmin", The Journal of Biological Chemistry, vol. 277, No. 36, pp. 33068-33074, 2002.

(56) References Cited

OTHER PUBLICATIONS

Veronese, "peptide and protein PEGylation: a review of problems and solutions", Biomaterials, vol. 22, pp. 405-417, 2001.

Wang, et al., "Human Plasminogen Catalytic Domain Undergoes an Unusual Conformational Change upon Activation", Journal Mol. Biol., vol. 295, pp. 903-914, 2000.

Weir, et al., "Formatting antibody fragments to mediate specific therapeutic functions", Biochemical Society Transactions, vol. 30, part 4, pp. 512-.

Wiman, et al., "On the Kinetics of the Reaction between Human Antiplasmin and a Low-Molecular-Weight Form of Plasmin", Eur. J. Biochem, vol. 87, pp. 143-146, 1978.

Wiman, et al., "On the Mechanism of the Reaction between Human $x_2$-Antiplasmin and Plasmin", The Journal of Biological Chemistry, vol. 254, No. 18, pp. 9291-9297, Sep. 25, 1979.

Wiman, et al., "On the Specific Interaction Between the Lysine-Binding Sites in Plasmin and Complementary Sites in $x_2$-Antiplasmin and in Fibrinogen", Biochimica and Biophysica Acta., vol. 579, pp. 142-154, 1979.

Yang, et al., "Tailoring structure-function and pharmacokinetic properties of single-chain Fv proteins by site-specific PEGylation", Protein Engineering, vol. 16, No. 10, pp. 761-770, 2003.

Zheng, et al., "PEGylation is effective in reducing immunogenicity, immunotoxicity, and hepatotoxicity of x-momorcharin in vivo", Immunopharmacology and Immunotoxicology, vol. 34, No. 5, pp. 866-873, 2012.

Butera, et al., "Characterization of a Reduced Form of Plasma Plasminogen as the Precursor for Angiostatin Formation", The Journal of Biological Chemistry, vol. 289, No. 5, pp. 2992-3000, Jan. 31, 2014.

Sawhney, et al., "PEGylation of Truncated Streptokinase Leads to Formulation of a Useful Drug with Ameliorated Attributes", PLOS One, pp. 1-21, May 18, 2016.

Jetrea, "Pediatric Postmarking Pharmacovigilance and Drug Utilization Review", Department of Health and Human Services, pp. 1-6, Jun. 2014.

\* cited by examiner

FIBRINOLYTIC COMPOSITION AND METHOD OF ITS PREPARATION

CROSS REFERENCES TO RELATED APPLICATIONS

This application is a national-stage application under 35 U.S.C. § 371 of International Application No. PCT/IN2020/050074, filed Jan. 23, 2020, which International Applications claims benefit of priority to Indian patent application No. 201911003104, filed Jan. 25, 2019.

FIELD OF THE INVENTION

The present invention relates to a fibrinolytic composition and method suitable for pharmaceutical use in thrombolytic therapies. The major aspect of the present invention is directed to a novel formulation comprising truncated and thiolated variants of plasmin conjugated site-specifically with PEG-moieties at various sites favorable for retention of activity over extended periods due to enhanced resistance against serpin-mediated inhibition that occurs in vivo, and thus are new drug candidates for the effective clot dissolution of pathological blood clots, especially scenarios where direct delivery of plasmin in the vicinity of a thrombus is the preferred option.

BACKGROUND OF THE INVENTION

The fibrinolytic system is primarily associated with removal of unwanted thrombi to maintain blood flow to the circulatory system. Fibrinolytic system regulates the activation of the zymogen, plasminogen into active plasmin, which further degrades fibrin into soluble fibrin degradation products. In addition, several distinct regulatory systems regulate the activation of plasminogen, activity of plasmin, and degradation of fibrin. (Collen, 1985; Collen et al., 1991). The pathologic formation of thrombi can produce significant consequences like embolism, ischemia, heart attack, stroke etc. Currently available thrombolytic treatments using plasminogen activators are associated with high general and/or cerebral bleeding risks, and a narrow therapeutic time window especially in case of ischemic strokes. Furthermore, the success of plasminogen activators and other thrombolytic agents in the therapy of thrombotic disease remains limited by intrinsic resistance of thrombi to fibrinolysis.

These issues arouse the attempts to design improved agents that would avoid bleeding complications and enhance thrombolytic potential (Khasa & Adivitiya, 2017). In particular, it would be desirable to overcome the fibrinolytic regulatory systems to achieve effective thrombolysis in such a way that the regulatory systems are at least partially maintained to minimize the risk of bleeding.

Direct fibrinolytic agents have potential for ameliorated thrombolytic therapy with enhanced hemostatic safety, therefore these can be considered as better futuristic approach to treat thrombotic disorders (Khasa & Adivitiya, 2017). Plasmin and its derivatives are 'direct-acting' thrombolytic agents which can degrade fibrin without involving the intermediate step of plasminogen activation, hence do not require free plasminogen. These are potent serine proteases involved in clot dissolution and are intrinsic in origin. Plasmin(ogen), a single-chain, glycoprotein (molecular mass of ~92 kDa), is the inactive precursor of plasmin (Robbins et al., 1967). Several plasmin(ogen) derivatives have been prepared for application as direct thrombolytics. Mini-plasmin(ogen) is a truncated form of plasmin(ogen), composed of the catalytic protease domain and the kringle 5 domain of plasminogen. A deletion mutant of plasminogen called delta plasminogen (TAL6003; Talecris Biotherapeutics, Inc.) composed of the kringle 1 and serine protease domain of plasminogen exhibits fibrinolytic potency comparable to plasmin (Hunt et al., 2008). Another plasmin(ogen) derivative, Micro-plasmin(ogen) (~29 kDa) is recombinant truncated form of plasmin(ogen), consists of only the catalytic domain which is functionally active. These truncated derivatives are more amenable to production by recombinant DNA technology.

The two main inhibitors of plasmin are $\alpha_2$-AP (plasma concentration of ~1 μM) and $\alpha_2$-macroglobulin (plasma concentration of ~3.4-3.7 μM) (Novokhatny, 2008). However, the ability of $\alpha_2$-macroglobulin to inhibit plasmin is much lower than that of $\alpha_2$-AP (Aoki, 2005). $\alpha_2$-antiplasmin is a key player in the fibrinolytic system. It is the fast serpin inhibitor of plasmin which forms a 1:1 stable complex with plasmin, either in the circulation or on the fibrin surface (Wiman & Collen, 1979). $\alpha_2$-AP is synthesized as a glycoprotein with a relative molecular mass of 70,000 Da. A partial X-ray crystal structure of murine $\alpha_2$-AP shows certain unique structural elements (Law et al., 2008). The protein has a long C-terminal sequence with a terminal lysine residue, which functions as a secondary binding site for free circulating plasmin and facilitates plasmin inactivation. Microplasmin is inactivated at a lower rate than intact plasmin, likely due to the absence of the lysine binding sites (Nagai et al., 2003). The second order rate constant of microplasmin inhibition of by $a_2$-antiplasmin is $2 \times 10^5$ mmol $L^{-1}$ $s^{-1}$, which is approximately 100 times slower than the inhibition rate of intact plasmin by $a_2$-antiplasmin ($2-4 \times 10^7$ mmol $L^{-1}s^{-1}$). The lower second order rate constant, corresponds to a half-life of microplasmin in circulating blood of 4 s, as compared to a half-life of 0.02 s (Nagai et al., 2003).

The effects and safety profile of plasmin and its truncated derivatives have been evaluated in several studies supported by in vivo evidences. When administered systemically, plasmin is rapidly neutralized within seconds by circulating $\alpha_2$-antiplasmin ($\alpha_2$-AP) and does not effectively dissolve the thrombus while also certainly not inducing hemorrhagic complications. It was concluded therefore that intravenous plasmin for thrombolytic therapy was safe but is not effective for clot dissolution (Ambrus et al., 1957; Clifton, 1957; Boyles et al., 1960; Jensen, 1976; Wiman et al., 1979; Nagai et al., 2001; Marder, 2011). Intravenous administration of microplasmin has been found to be associated with reduction in infarct size and has a lower propensity to cause bleeding than recombinant t-PA in various pre-clinical acute stroke models (Nagai et al., 1999; Lapchak et al., 2002; Suzuki et al., 2004). Microplasmin has been demonstrated to be well tolerated in healthy young, and old individuals. But intravenous delivery of microplasmin does not result in effective thrombolysis due to its ultra-fast inactivation by circulating inhibitors in similar manner as plasmin even though slower. In contrast, successful thrombolysis and reperfusion has been achieved with catheter-directed administration of plasmin and microplasmin. Catheter-delivered plasmin is comparable to tissue plasminogen activator (t-PA) for local thrombolysis in a rabbit abdominal aorta thrombosis model while minimizing bleeding potential (Marder et al., 2001). According to this strategy, plasmin administered by catheter binds to thrombus, where it is shielded from $\alpha_2$-antiplasmin and induces thrombolysis causing lesser bleeding tendency (Marder et al., 2001).

A study employing truncated plasmin Δ(K2-K5) in middle cerebral artery occlusion model via local infusion suggests that Δ(K2-K5) plasmin treatment even at the highest dose offers at least a 5-fold superior safety margin than the lowest dose of rt-PA. Moreover, Δ(K2-K5) plasmin showed neuro-protective outcome as it significantly reduces infarct volume and improves behavior (Crumrine et al., 2012).

Intracranial hemorrhage safety profile of recombinant microplasmin was also assessed in rats and rabbits. Surprisingly, microplasmin showed potential as neuro-protective agent by virtue of its tendency to reduce infarct volume and improve behavioral rating scores in embolized rabbits (Lapchak et al., 2002). Local delivery of microplasmin over 2 h, induces approximately 50% clot lysis in extracorporeal loop thrombosis model in rabbits, without protracting the bleeding times. Also it reduces focal cerebral infarction in mice ischemic stroke model, when administered within several hours after middle cerebral artery (MCA) occlusion (Nagai et al., 2003).

$\alpha_2$-antiplasmin appears to limit the success of direct thrombolytic agents by making it difficult to achieve efficient clot lysis. Various reports document that transient depletion of $\alpha_2$-AP activity may lead to enhanced endogenous fibrinolytic activity (Pakola et al., 2009; Thijs et al., 2009). Clots from $\alpha_2$-antiplasmin-deficient patients undergo spontaneous lysis even when those clots are suspended in plasma containing normal levels of free $\alpha_2$-antiplasmin (Sakata & Aoki, 1982). Thus, Fibrin bound α2-antiplasmin is a critical inhibitor of clot lysis. The specific inhibition of clot-bound $\alpha_2$-antiplasmin with monoclonal antibodies (mAbs) against $\alpha_2$-antiplasmin can significantly amplify thrombolysis (Reed et al., 1990; Reed, 1997). Moreover, effective thrombolysis can be achieved by neutralizing $\alpha_2$-AP activity through the use of $\alpha_2$-AP antibodies ($\alpha_2$AP-I) which bind to both circulating as well fibrin-bound $\alpha_2$-AP (Singh et al., 2017). High levels of circulating $\alpha_2$-AP increase brain infarction and interfere with the dissolution of cerebral thromboemboli in mice (Reed et al., 2014). However, depletion of $\alpha_2$-AP by administration of microplasmin, plasmin or polyclonal antibodies enhances endogenous fibrinolysis in downstream areas of secondary thrombosis thus, significantly improving the stroke outcome reduced ischemic brain injury in different animal stroke models. $\alpha_2$-antiplasmin inactivation is significantly more effective than tissue plasminogen activator at reducing brain infarction, hemorrhage and mortality (Nagai et al., 2001; Reed et al., 2014). Intra-vitreal microplasmin administration for non-thrombolytic use has been approved by FDA in 2012 for the treatment of symptomatic vitreomacular adhesion (VMA) or causing total posterior vitreous detachment (PVD) Chen et al., 2008; de Smet et al., 2009). The drug has been produced in *P. pastoris* and is marketed commercially under the trade name of Jetrea (ocriplasmin, ThromboGenics, Inc.) (US Food and Drug Administration, 2016)

In view of preclinical reports, plasmin and its derivative have shown encouraging outcomes with improved benefit/risk ratio as compared to available thrombolytics. However, despite possessing a higher efficacy, potential neuro-protective properties and positive safety profile, the rapid inhibition of plasmin/microplasmin by $\alpha_2$-AP hampers their successful development as effective thrombolytics.

To circumvent these impediments, attempts are highly desirable so as to target $\alpha_2$-antiplasmin in such a manner that its regulatory mechanism is partly maintained to prevent unwanted bleeding risks. In the context of the situation, 'direct-acting' fibrinolytic agents with protection against $\alpha_2$-antiplasmin will brighten the prospects of thrombolytic therapy which further entails a thorough understanding of the substrate-inhibitor interaction mechanism. A study by Turner et al., 2002 provides a structural insight into the antiplasmin-plasmin interaction system. They showed that chimerization of protease domain loops with those of factor D, a component of the complement system, did not significantly alter the fibrinolytic ability of microplasmin, but provided resistance towards $\alpha_2$-antiplasmin (Turner et al., 2002). However, the substitution of heterologous domains and a non-natural chimeric polypeptide potentially creates further hurdles to the development of an effective and immunologically inert drug candidate.

Conjugating biomolecules with polyethylene glycol (PEG) is an established method to modulate their molecular interactions. Protein-PEGylation has been clinically proven to enhance the circulation half-life of protein-based therapeutics (Bailon & Berthold, 1998; Greenwald et al., 2003; Fishburn, 2008; Milla et al., 2012; Zheng et al., 2012; Qimeng et al., 2013). The covalent attachment of polyethylene glycol (PEG) to proteins enhances their hydrodynamic size. Because PEG tail is quite a flexible moiety, it can also act to shield protein sites from recognition by the immune system, cellular receptors, or proteases.

These properties lead to decreased renal, enzymatic, and cellular clearance, resulting in prolonged circulation half-lives in the bloodstream (Chapman et al., 1999; Chapman, 2002). PEG (Polyethylene glycol) has been approved by the Food and Drug Administration (FDA) (Gaberc-Porekar et al., 2008). Numerous strategies based on activated PEG are available to provide coupling of PEG moiety to one or more residues on the protein or peptide. Although the technique of PEG-coupling is generic, but discreet positioning of PEG moiety in a therapeutic protein is eminently important. Generally, it is known that properties such as biological activity and half-life of conjugated protein depend on the site of modification and the size of PEG-group (Veronese, 2001; Harris & Veronese, 2003). Several studies suggest that long PEG chains can stabilize proteins by interacting with the protein surface and reducing the solvent accessible surface area, or by introducing molecular crowding (excluded volume effect) to slow down the unfolding rate of the host protein (Meng et al., 2012; Hamed et al., 2013; Pandey et al., 2013). Conjugation of 10 kDa PEG to trypsin improves its thermal stability while maintaining the bioactivity under physiological conditions (Chiu et al., 2010). However, reduction or even loss of bioactivity can be an unexpected side effect of PEGylation if it sterically restrains ligand-receptor binding (Chapman, 2002; Weir et al., 2002). Therefore, site-specific PEGylation techniques are developed (King et al., 1994; Harris & Chess, 2003), in which the PEG molecule is attached to the protein at a specific residue that can be engineered at a position distal to the target-binding region of the protein. Cysteine-specific conjugation of PEG-maleimide to GCSF increases the half-life of the molecule (Hao, et al., 2006). PEGylation of cysteine mutant of staphylokinase was able to achieve enhanced circulatory half-life while maintaining its thrombolytic potency (Collen et al., 2000). The utility of site-specific PEGylation for creating highly potent, long-acting GM-CSF analogs was demonstrated in rats to achieve up to 47-fold longer circulating half-lives of pegylated forms than wild type GM-CSF (Doherty et al., 2005). Site-specific PEGylation of a thrombomodulin (TM) derivative at the C terminus does not affect its enzymatic activity (Cazalis et al., 2004). It has been shown that coupling of PEG polymer is able to reduce protein protein interactions between therapeutics, proteins, and cells in vivo (Mok et al., 2005). PEGylation of cofactor altered the interactions between the enzyme and modified cofactors by affecting the rate of formation of enzyme/cofactor complexes and/or the formation of enzyme/cofactor/substrate complexes (Ozbakir & Banta, 2018).

Therefore, there is a need for better fibrinolytic composition to achieve faster clot dissolution without inhibition by their physiological inhibitors.

Objective of the Invention

An object of the present invention is to provide a plasmin(ogen) variant polypeptide comprising substitution of amino acid residues with a cysteine residue in the plasmin(ogen) catalytic domain.

Another object of the present invention is to provide a plasmin(ogen) variant polypeptide comprising substitution of amino acid residues with a cysteine residue in the plasmin(ogen) catalytic domain, wherein the cysteine residues are covalently modified with thiol-reactive polyethylene glycol (PEG) moiety.

Yet another object of the present invention is to provide a plasmin(ogen) variant polypeptide comprising substitution of amino acid residues with a cysteine residue in the plasmin(ogen) catalytic domain, said plasmin(ogen) variant polypeptide being insensitive to alpha2-antiplasmin mediated inhibition.

Still another object of the present invention is to provide a plasmin(ogen) variant polypeptide comprising substitution of amino acid residues with a cysteine residue in the plasmin(ogen) catalytic domain for prolonging the clot lysis time by retarding or inhibiting alpha2-antiplasmin mediated inhibition.

SUMMARY OF THE INVENTION

Accordingly, an aspect of the present invention provides a fibrinolytic composition comprising:
a. a modified thiol derivative of plasminogen having substitution of one to eight amino acid residues of SEQ ID NO. 2 with a cysteine residue; and
b. a pharmaceutically acceptable diluent, carrier, or adjuvant.

Another aspect of the present invention provides a plasmin(ogen) variant polypeptide comprising substitution of one to eight amino acid residues of amino acid sequence as set forth in SEQ ID NO: 2, wherein the amino acid residue substituted with a cysteine residue is selected from the amino acid sequences EVNLEPHV (amino acids 81-88 of SEQ ID NO: 2), GTF, AG, FGM and EKS of plasmin(ogen) catalytic domain.

Another aspect of the present invention provides a plasmin (ogen) variant polypeptide comprising substitution of one to eight amino acid residues of amino acid sequence as set forth in SEQ ID NO. 2, wherein the amino acid residue substituted with a cysteine residue is selected from the amino acid sequence EVNLEPHV (amino acids 81-88 of SEQ ID NO: 2) of plasmin (ogen) catalytic domain.

Still another aspect of the present invention provides a plasmin(ogen) variant polypeptide consisting of cysteine substitution, wherein the amino acid sequences with substitution are as set forth in E81C (SEQ ID NO. 3), V82C (SEQ ID NO. 4), N83C (SEQ ID NO. 5), L84C (SEQ ID NO. 6), E85C (SEQ ID NO. 7), P86C (SEQ ID NO. 8), H87C (SEQ ID NO. 9), V88C (SEQ ID NO. 10) E85C-H87C (SEQ ID NO. 11), and V82C-H87C (SEQ ID NO. 12).

Yet another aspect of the present invention provides a plasmin(ogen) variant polypeptide comprising substitution of one to three amino acid residues of amino acid sequence as set forth in SEQ ID NO. 2, wherein the amino acid residue substituted with a cysteine residue is selected from the amino acid sequence GTF of plasmin(ogen) catalytic domain.

Another aspect of the present invention provides a plasmin(ogen) variant polypeptide consisting of cysteine substitution, wherein the amino acid sequences with substitution are as set forth in G148C (SEQ ID NO. 13), T149C (SEQ ID NO. 14), and F150C (SEQ ID NO. 15).

Still another aspect of the present invention provides a plasmin(ogen) variant polypeptide comprising substitution of one to two amino acid residues of amino acid sequence as set forth in SEQ ID NO. 2, wherein the amino acid residue substituted with a cysteine residue is selected from the amino acid sequence AG of plasmin(ogen) catalytic domain.

Yet another aspect of the present invention provides a plasmin(ogen) variant polypeptide consisting of cysteine substitution, wherein the amino acid sequences with substitution are as set forth in A189C (SEQ ID NO. 16), and G190C (SEQ ID NO. 17).

Another aspect of the present invention provides a plasmin(ogen) variant polypeptide comprising substitution of one to three amino acid residues of amino acid sequence as set forth in SEQ ID NO. 2, wherein the amino acid residue substituted with a cysteine residue is selected from the amino acid sequence FGM of plasmin(ogen) catalytic domain.

Still another aspect of the present invention provides a plasmin(ogen) variant polypeptide consisting of cysteine substitution, wherein the amino acid sequences with substitution are as set forth in F41C (SEQ ID NO. 18), G42C (SEQ ID NO. 19), and M43C (SEQ ID NO. 20).

Yet another aspect of the present invention provides a plasmin(ogen) variant polypeptide comprising substitution of one to three amino acid residues of amino acid sequence as set forth in SEQ ID NO. 2, wherein the amino acid residue substituted with a cysteine residue is selected from the amino acid sequence EKS of plasmin(ogen) catalytic domain.

Another aspect of the present invention provides a plasmin(ogen) variant polypeptide consisting of cysteine substitution, wherein the amino acid sequences with substitution are as set forth in E64C (SEQ ID NO. 21), K65C (SEQ ID NO. 22), and S66C (SEQ ID NO. 23).

Still another aspect of the present invention provides a plasmin(ogen) variant polypeptide consisting at least 2, 3 and 8 consecutive or alternate or random substitution of amino acid residues of catalytic domain of plasmin(ogen) with cysteine.

Yet another aspect of the present invention provides a plasmin(ogen) variant polypeptide further comprising covalently modified thiol groups at one or more substituted cysteine residues.

Another aspect of the present invention provides a plasmin(ogen) variant polypeptide wherein said polypeptide is covalently modified with thiol-reactive polyethylene glycol (PEG) moiety.

Still another aspect of the present invention provides a plasmin(ogen) variant polypeptide covalently modified with thiol-reactive polyethylene glycol (PEG) moiety, wherein the polyethylene glycol moiety is a linear or a branched polymer of varying molecular size ranging from about 5 kDa to about 40 kDa.

Yet another aspect of the present invention provides a plasmin(ogen) variant polypeptide, wherein said polypeptide is insensitive to alpha2-antiplasmin mediated inhibition.

Another aspect of the present invention provides a pharmaceutical composition comprising the covalently modified plasmin(ogen) variant polypeptide for prolonging the clot lysis time by retarding or inhibiting alpha2-antiplasmin mediated inhibition.

BRIEF DESCRIPTION OF FIGURES

FIGS. 1A, 1B, and 1C are ribbon diagrams of the functional domain of human plasminogen shown in complex with $\alpha_2$-antiplasmin predicted using GRAMM-X Protein-Protein Docking Web Server v.1.2.0. The available structural information was used to interpret interaction interface between functional domain of human plasminogen (Wang et al., 2000) and $\alpha_2$-antiplasmin (Law et al., 2008) which was further used to design modified derivatives. The fragments (red, yellow, blue, orange and purple) in micro-plasminogen structure (green) represents the selected residues for site-specific covalent modification which are quite far away from the activation cleavage site (magenta). FIG. 1D, blue beads are schematic presentation of PEG polymers attached at one of the selected locations on micro-plasminogen.

FIG. 2A is a strategy for cloning and expression of plasminogen catalytic domain has been outlined. DNA sequence coding for catalytic domain (micro-plasminogen) was amplified from Human Plasminogen cDNA using Primers with NdeI and Hind III restriction sites and sub cloned into the pET11a vector digested with same set of restriction endonucleases. FIG. 2B is an agarose gel picture showing site-directed mutagenesis of micro-plasminogen. Lane 1. Wild-type micro-plasminogen; Lane 2. Ladder; Lane 3 to 7 PCR products of site-directed mutagenesis.

In FIG. 5A Cation-exchange purified fractions of PEGylated variant shows two bands corresponding to PEG-conjugated protein and the un-reacted part respectively. In FIG. 5B, PEG-conjugated protein was separated from the un-reacted fraction by size-exclusion chromatography. The SDS-PAGE confirms the homogeneity of the purified PEGylated protein.

FIG. 7A shows time dependence of wild-type plasmin/micro-plasmin inhibition by $\alpha_2$-antiplasmin. The graphs of FIGS. 7B and 7C show the influence of PEGylation on the inhibition by $\alpha_2$-antiplasmin. FIG. 7B shows residual activity of Mono-PEGylated variants with different PEG sizes. FIG. 7C shows residual activity of Mono-PEGylated and Bi-PEGylated variants with different PEG sizes. Wild-type or PEGylated micro-plasmins were added to cuvettes containing antiplasmin in 100 mM sodium phosphate, pH 7.2 and 0.5% BSA. The reaction mixture was incubated at 25° C. for the time interval ranging 15 sec-30 minutes and the change in absorbance at 405 nm was recorded at 60 s intervals after addition of 0.5 mM Chromozym® PL. The residual enzyme activity was measured at different intervals from the slope of the curve and plotted as log residual activity versus time. The linear fits of the data are shown in the activity plot (Wiman et al., 1978; Turner et al., 2002). The initial value of activity was defined as 100%.

DETAILED DESCRIPTION OF INVENTION

Figure 1A:
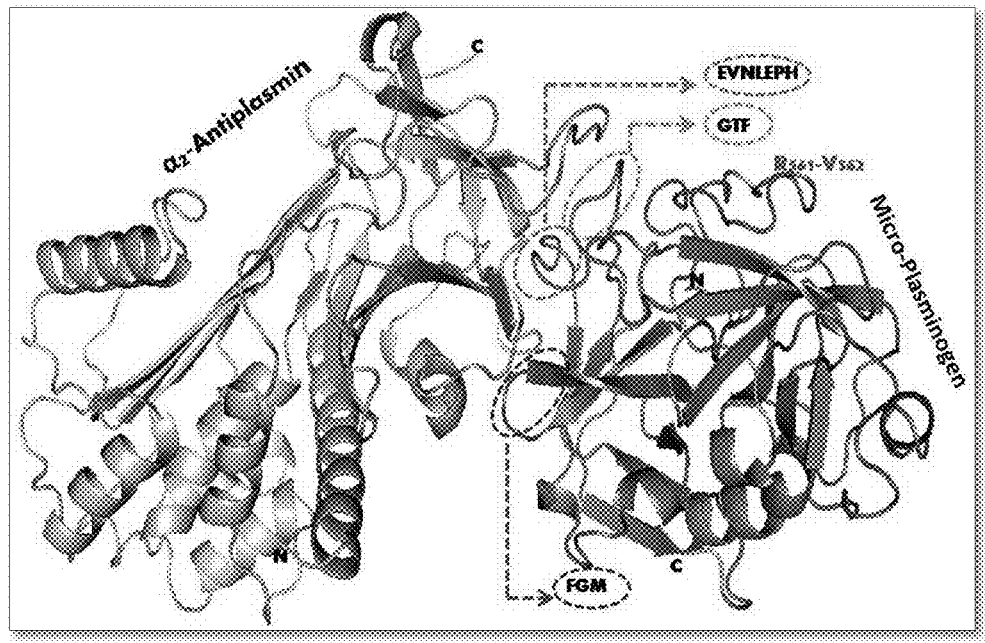
FIGS. 1A-1D show a Scheme of covalent modification.
Figure 1B:
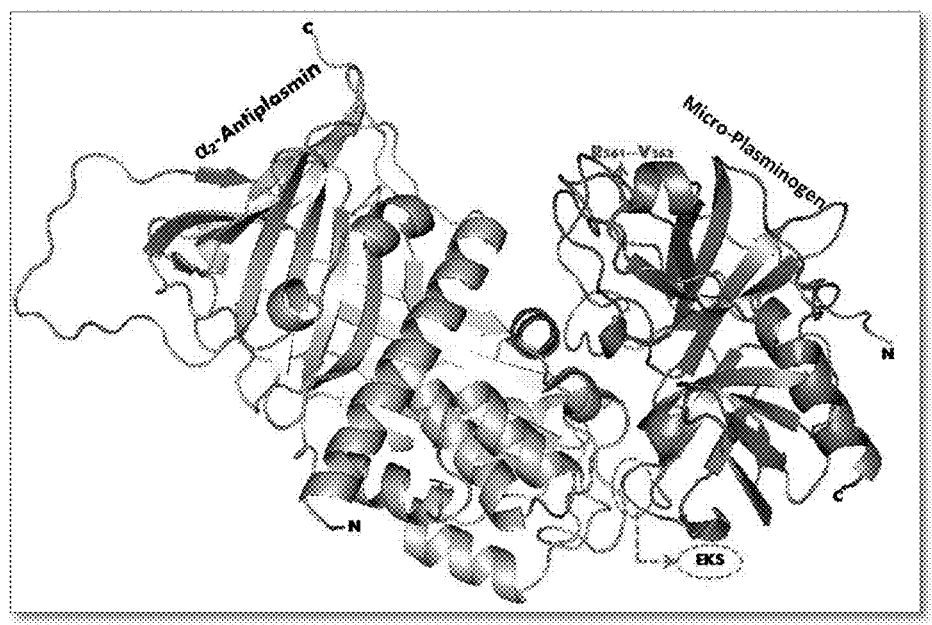
Figure 1C:
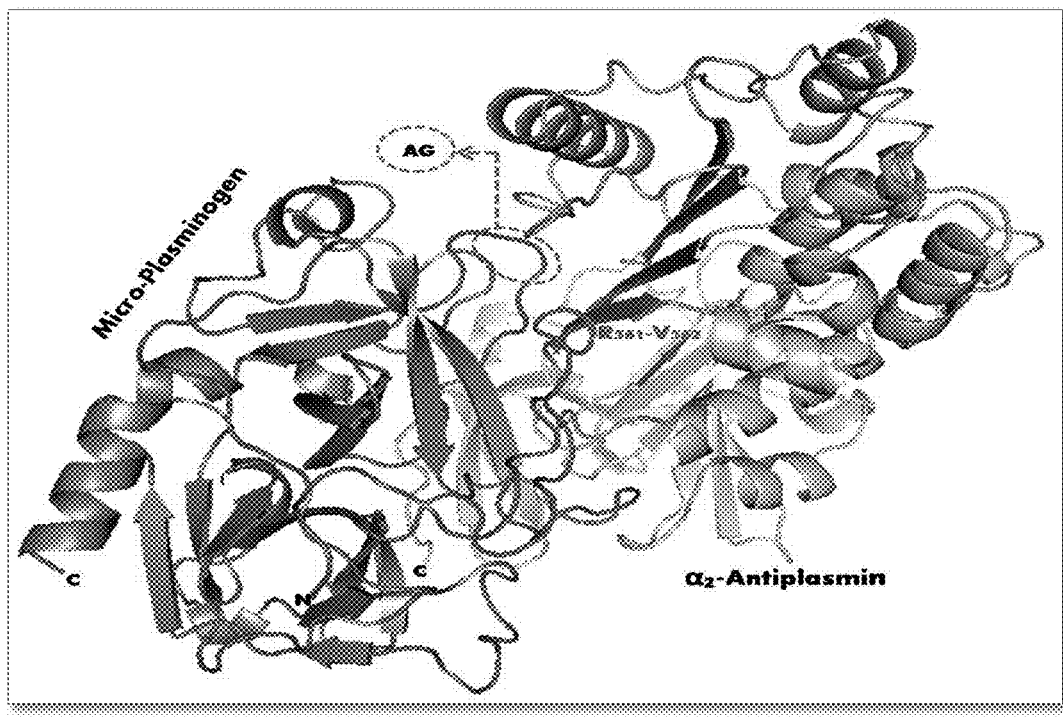
Figure 1D:
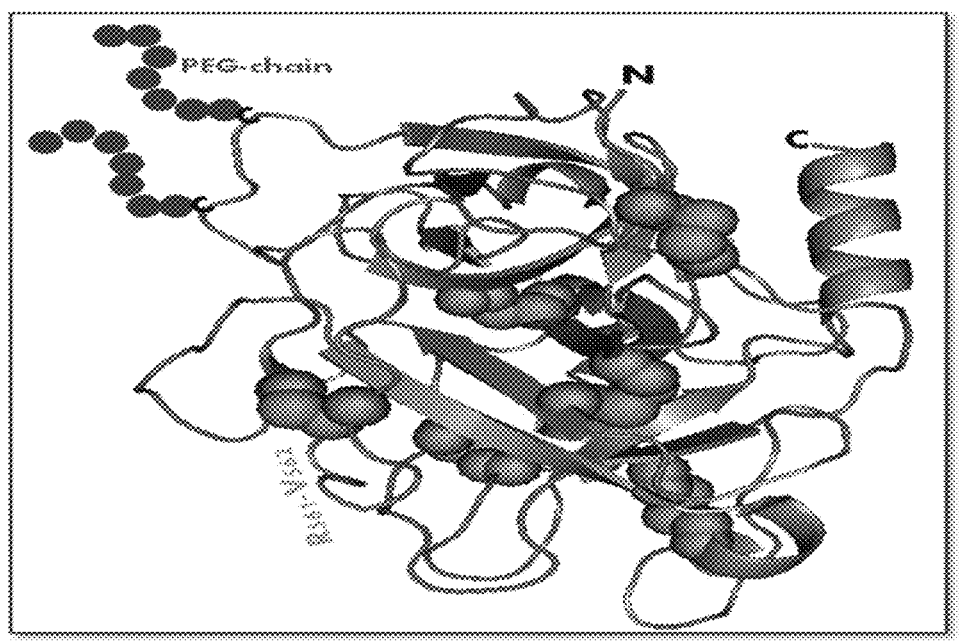

The present invention discloses an approach to address the problems associated with the development of direct-acting thrombolytics having desirable therapeutic profile. The invention relates to recombinant analogues of plasminogen-derivative as well as their PEGylated counterparts. The catalytic domain of plasmin(ogen) has been altered by cysteine mutation of one or more amino acids in its primary sequence. Further, a PEG moiety is covalently coupled to the free cysteine residues incorporated in its catalytic domain. The invention describes the method of conjugating thiol reactive PEG to biologically active plasminogen derivative and process involving purification of these PEG-conjugated plasminogen derivatives. Furthermore, the invention exemplifies the in vitro activity of modified plasmin variants against $\alpha_2$-antiplasmin.

An embodiment of the present invention provides a fibrinolytic composition comprising:
 a. a modified thiol derivative of plasminogen having substitution of one to eight amino acid residues of SEQ ID NO. 2 with a cysteine residue; and
 b. a pharmaceutically acceptable diluent, carrier, or adjuvant.

In an embodiment of the present invention, there is provided a fibrinolytic composition, wherein the substitutions are done in regions comprising of sequences selected from the group having sequences EVNLEPHV (amino acids 81-88 of SEQ ID NO: 2), GTF, AG, FGM, and EKS.

In another embodiment of the present invention, there is provided a fibrinolytic composition, wherein the cysteine substitution in span EVNLEPHV (amino acids 81-88 of SEQ ID NO: 2) is done at a position selected from the group consisting of E81C (SEQ ID NO. 3), V82C (SEQ ID NO. 4), N83C (SEQ ID NO. 5), L84C (SEQ ID NO. 6), E85C (SEQ ID NO. 7), P86C (SEQ ID NO. 8), H87C (SEQ ID NO. 9), V88C (SEQ ID NO. 10) E85C-H87C (SEQ ID NO. 11), and V82C-H87C (SEQ ID NO. 12).

In yet another embodiment of the present invention, there is provided a fibrinolytic composition, wherein the cysteine substitution in span GTF is done at a position selected from the group consisting of G148C (SEQ ID NO. 13), T149C (SEQ ID NO. 14), and F150C (SEQ ID NO. 15).

In still another embodiment of the present invention, there is provided a fibrinolytic composition, wherein the cysteine substitution in span AG is done at a position selected from the group consisting of A189C (SEQ ID NO. 16), and G190C (SEQ ID NO. 17).

In another embodiment of the present invention, there is provided a fibrinolytic composition, wherein the cysteine substitution in span FGM is done at a position selected from the group consisting of F41C (SEQ ID NO. 18), G42C (SEQ ID NO. 19), and M43C (SEQ ID NO. 20).

In yet another embodiment of the present invention, there is provided a fibrinolytic composition, wherein the cysteine substitution in span EKS is done at a position selected from the group consisting of E64C (SEQ ID NO. 21), K65C (SEQ ID NO. 22), and S66C (SEQ ID NO. 23).

In still another embodiment of the present invention, there is provided a fibrinolytic composition, wherein the modified thiol derivative of plasminogen is covalently modified with thiol-reactive polyethylene glycol (PEG) moiety which is linear or branched polymer having varying molecular size from 5 kDa to 40 kDa.

Another embodiment of the present invention provides a use of the fibrinolytic composition for prolonging the clot lysis time by retarding or inhibiting alpha2-antiplasmin mediated inhibition.

Yet another embodiment of the present invention provides a plasmin(ogen) variant polypeptide comprising substitution of one to eight amino acid residues of amino acid sequence as set forth in SEQ ID NO: 2 useful as a therapeutic agent.

An embodiment of the present invention provides a plasmin(ogen) variant polypeptide comprising substitution of one to eight amino acid residues of amino acid sequence as set forth in SEQ ID NO: 2, wherein the amino acid residue substituted with a cysteine residue is selected from the amino acid sequences EVNLEPHV (amino acids 81-88 of SEQ ID NO: 2), GTF, AG, FGM and EKS of plasmin(ogen) catalytic domain.

In yet another embodiment of the present invention, there is provided a plasmin(ogen) variant polypeptide comprising substitution of one to eight amino acid residues of amino acid sequence as set forth in SEQ ID NO. 2, wherein the amino acid residue substituted with a cysteine residue is selected from the amino acid sequence EVNLEPHV (amino acids 81-88 of SEQ ID NO: 2) of plasmin(ogen) catalytic domain.

In still another embodiment of the present invention, there is provided a plasmin(ogen) variant polypeptide consisting of cysteine substitution, wherein the amino acid sequences with substitution are as set forth in E81C (SEQ ID NO. 3), V82C (SEQ ID NO. 4), N83C (SEQ ID NO. 5), L84C (SEQ ID NO. 6), E85C (SEQ ID NO. 7), P86C (SEQ ID NO. 8), H87C (SEQ ID NO. 9), V88C (SEQ ID NO. 10) E85C-H87C (SEQ ID NO. 11), and V82C-H87C (SEQ ID NO. 12).

In another embodiment of the present invention, there is provided a plasmin(ogen) variant polypeptide comprising substitution of one to three amino acid residues of amino acid sequence as set forth in SEQ ID NO. 2, wherein the amino acid residue substituted with a cysteine residue is selected from the amino acid sequence GTF of plasmin(ogen) catalytic domain.

In yet another embodiment of the present invention, there is provided a plasmin(ogen) variant polypeptide consisting of cysteine substitution, wherein the amino acid sequences with substitution are as set forth in G148C (SEQ ID NO. 13), T149C (SEQ ID NO. 14), and F150C (SEQ ID NO. 15).

In still another embodiment of the present invention, there is provided a plasmin(ogen) variant polypeptide comprising substitution of one to two amino acid residues of amino acid sequence as set forth in SEQ ID NO. 2, wherein the amino acid residue substituted with a cysteine residue is selected from the amino acid sequence AG of plasmin(ogen) catalytic domain.

In another embodiment of the present invention, there is provided a plasmin(ogen) variant polypeptide consisting of cysteine substitution, wherein the amino acid sequences with substitution are as set forth in A189C (SEQ ID NO. 16), and G190C (SEQ ID NO. 17).

In yet another embodiment of the present invention, there is provided a plasmin(ogen) variant polypeptide comprising substitution of one to three amino acid residues of amino acid sequence as set forth in SEQ ID NO. 2, wherein the amino acid residue substituted with a cysteine residue is selected from the amino acid sequence FGM of plasmin(ogen) catalytic domain.

In still another embodiment of the present invention, there is provided a plasmin(ogen) variant polypeptide consisting of cysteine substitution, wherein the amino acid sequences with substitution are as set forth in F41C (SEQ ID NO. 18), G42C (SEQ ID NO. 19), and M43C (SEQ ID NO. 20).

In another embodiment of the present invention, there is provided a plasmin(ogen) variant polypeptide comprising substitution of one to three amino acid residues of amino acid sequence as set forth in SEQ ID NO. 2, wherein the amino acid residue substituted with a cysteine residue is selected from the amino acid sequence EKS of plasmin(ogen) catalytic domain.

In yet another embodiment of the present invention, there is provided a plasmin(ogen) variant polypeptide consisting of cysteine substitution, wherein the amino acid sequences with substitution are as set forth in E64C (SEQ ID NO. 21), K65C (SEQ ID NO. 22), and S66C (SEQ ID NO. 23).

In another embodiment of the present invention, there is provided a plasmin(ogen) variant polypeptide consisting of cysteine substitution, wherein the amino acid sequences with substitution are as set forth in E81C (SEQ ID NO. 3), V82C (SEQ ID NO. 4), N83C (SEQ ID NO. 5), L84C (SEQ ID NO. 6), E85C (SEQ ID NO. 7), P86C (SEQ ID NO. 8), H87C (SEQ ID NO. 9), V88C (SEQ ID NO. 10) E85C-H87C (SEQ ID NO. 11), V82C-H87C (SEQ ID NO. 12), G148C (SEQ ID NO. 13), T149C (SEQ ID NO. 14), F150C (SEQ ID NO. 15), A189C (SEQ ID NO. 16), G190C (SEQ ID NO. 17), F41C (SEQ ID NO. 18), G42C (SEQ ID NO. 19), M43C (SEQ ID NO. 20), E64C (SEQ ID NO. 21), K65C (SEQ ID NO. 22), and S66C (SEQ ID NO. 23).

In still another embodiment of the present invention, there is provided a plasmin(ogen) variant polypeptide consisting at least 2, 3 and 8 consecutive or alternate or random substitution of amino acid residues of catalytic domain of plasmin(ogen) with cysteine.

In another embodiment of the present invention, there is provided a plasmin(ogen) variant polypeptide further comprising covalently modified thiol groups at one or more substituted cysteine residues.

In yet another embodiment of the present invention, there is provided a plasmin(ogen) variant polypeptide wherein said polypeptide is covalently modified with thiol-reactive polyethylene glycol (PEG) moiety.

In still another embodiment of the present invention, there is provided a plasmin(ogen) variant polypeptide covalently modified with thiol-reactive polyethylene glycol (PEG) moiety, wherein the polyethylene glycol moiety is a linear or a branched polymer of varying molecular size ranging from about 5 kDa to about 40 kDa.

In another embodiment of the present invention, there is provided a plasmin(ogen) variant polypeptide, wherein said polypeptide is insensitive to alpha2-antiplasmin mediated inhibition.

Another embodiment of the present invention provides a pharmaceutical composition comprising the covalently modified plasmin(ogen) variant polypeptide for prolonging the clot lysis time by retarding or inhibiting alpha2-antiplasmin mediated inhibition.

The selection of appropriate sites for surface modification is a critical step to maintain the functionality of the modified variants. Several strategies have been developed for protein PEGylation, but the rare occurrence of free cysteine residues in proteins makes thiol based chemistry a more selective approach for PEG-conjugation. Cysteine contains a potentially reactive sulph-hydryl/thiol (—SH) group (Veronese, 2002; Grace et al., 2005). Furthermore, cysteines are commonly present as disulphides, considered to be responsible for maintaining the folding and stability of proteins, hence preserving the bioactive conformation essential for its biological activity (Roberts, 2002). The kringle-less derivative of plasminogen contains twelve cysteine residues, all of which are engaged in six disulphide linkages. Since none of intrinsic cysteines are free in natively folded micro-plasminogen (Peterson et al. 1990), this offers a unique opportunity to strategically incorporate an unpaired cysteine into the micro-plasminogen which will be available free for PEG-coupling provided the cysteine incorporation is tolerated without disruption of catalytic activity. The technique of in vitro mutagenesis allows incorporation of a non-native, free cysteine residue into protein which can offer the benefit of selecting the target site for modification to obtain desired results without unwanted side effects.

The molecular surface of the catalytic domain of plasminogen consists of several distinct surface-exposed loops (Wang et al., 2000). The surface-loops among different serine proteases are considered to be important for their selective interactions with substrates and inhibitors (Madison et al., 1989; Wang et al., 2000). The residues were selected on the basis of surface accessibility and association with $\alpha_2$-AP using available structural information. The X-ray crystal structure of human antiplasmin ($\alpha_2$-AP) has not been solved yet. But the crystal structure of murine antiplasmin is known (Law et al., 2008), which shares ~78.47% sequence similarity with human plasminogen. The three dimensional structure models of micro-plasminogen in complex with murine $\alpha_2$-antiplasmin was predicted using the available structural information of human plasminogen catalytic domain (Wang et al., 2000) as well as murine antiplasmin. The docking models generated by GRAMM-X Protein-Protein Docking Web Server v.1.2.0 (Tovchigrechko and Vakser, 2006) were analyzed using PyMOL graphic visualization system and used to interpret potential interface residues between these two proteins.

Five different locations consisting of two to eight residues were chosen by keeping it in mind that selected sites are distant from the catalytic site as well as the native cysteines of protein involved in disulfide linkage so that there is expected to be little interference with the fibrinolytic abilities [FIG. 1]. These sites include FGM (583-585); EKS (606-608); EVNLEPHV (623-630); GTF (690-692); AG (731-732) of SEQ ID NO: 1.

The present invention provides a method for development of improved thrombolytic molecules to treat ischemic stroke and other thrombotic diseases. Because $\alpha_2$-antiplasmin is a fast covalent inhibitor of plasmin and its derivatives, it makes them inefficient for clot dissolution. Therefore, the specific object of the present invention is to provide partial protection to plasmin or its derivatives from ultrafast inactivation by plasma inhibitors, thereby speeding up the fibrinolysis process and making it more effective. The present invention describes construction of eight cysteine analogs of truncated plasminogen derivatives, primarily in the regions of the protein that are associated in interaction with $\alpha_2$-antiplasmin, as also those regions that lie relatively away from the major activation sites. Further, the invention illustrates the effect of covalent grafting of single 20 kDa/40 kDa PEG chain (i.e. mono-PEGylation) and also the double (i.e. bi-PEGylation) sites in the protein, on $\alpha_2$-antiplasmin mediated inhibition of truncated plasmin derivatives. The present invention further discloses that the covalently modified plasmin variants obtained by site-specific PEGylation exhibit a markedly reduced inhibition rate relative to the wild type/unmodified/native plasmin variant. The explanation to the successful protein resistance properties of PEG attached to the surface is the flexibility and mobility of PEG chains as flexible PEG moiety that sterically interfered with the recognition of $\alpha_2$-antiplasmin interacting sites. In addition, the correlation of the number of conjugation sites, size of PEG group and their effect on $\alpha_2$-antiplasmin inhibition was determined. Bi-PEGylation i.e. attachment of 20 kDa-PEG at two different sites in plasmin derivative molecule contributes to its relatively longer activity than the mono-PEGylated ones as the cumulative shielding effect of PEG is greater that affects the interaction between $\alpha_2$-antiplasmin and modified plasmin derivatives in more significant manner. Furthermore, the present invention describes that modified conjugates retain their characteristic amidolytic properties. The kinetic parameters revealed that both the free cysteine variants and their covalently modified forms were quite equivalent to their natural counterparts, showing comparable amidolysis of small molecular weight chromogenic substrate (chromozyme PL). The present invention provides a method for achieving efficient clot lysis by prolonging the $\alpha_2$-antiplasmin mediated inhibition of plasmin derivative as the long half-life will allow the persistence of effect. The combined effects of native plasmin activity and retardation of $\alpha_2$-antiplasmin mediated inhibition helps to facilitate faster clot dissolution. This new functional attribute of lesser antiplasmin sensitivity imparted to plasmin variants makes it a distinctly promising molecule for the treatment thrombotic disorders.

The primary attributes such as self-sustaining mechanism (plasminogen-independent pathway of fibrin degradation) combined with enhanced $\alpha_2$-antiplasmin resistance makes modified plasmin derivatives a promising candidate for the development of efficacious thrombolytic agents.

EXAMPLES

Materials

The cloning of truncated plasminogen derivative (catalytic domain) was done in T7 RNA polymerase inducible promoter based expression vector pET11a and transformed into expression host *E. coli* strain BL21(DE3) procured from Novagen Inc. (Madison, Wisconsin, USA). All the DNA modifying enzymes including restriction enzymes, T4 DNA Ligases and thermostable DNA polymerase used in gene cloning experiments were purchased from New England Biolabs (Beverly, Massachusetts) or Promega Inc. (Madison, Wisconsin, USA). *E. coli* XL1-Blue cloning host and the QuickChange™ Site-Directed Mutagenesis Kit were obtained from Stratagene Inc. (La Jolla, California). Commercially available kits from Qiagen (GmbH, Germany) were used for isolation of plasmid and extraction of the DNA or for retrieving the PCR amplified DNA from agarose gel. All the oligonucleotide primers used in the study for cloning and mutagenesis were custom synthesized from the Integrated DNA Technologies (IDT), USA. DNA sequencing was performed on an automated sequencer (ABI PRISM 377 DNA Sequencer, Perkin Elmer Applied Biosystems). Protein purification resins such as SP-Sepharose™ (Fast Flow) and Superdex™-75 pg were procured from GE-Amersham Biosciences. FPLC was performed on the sophisticated chromatographic purification pump AKTA Purifier™, GE Healthcare, USA. Absorption spectroscopic measurements were carried out on Lambda 35 Perkin-Elmer UV/Vis spectrophotometer. All the materials required for the SDS-PAGE were purchased from Bio-RAD, USA. Superior quality methoxy-PEG maleimide reagent (10 kDa to 40 kDa) was purchased from JenKem Technology, USA. Zeba™ Spin Desalting columns used for protein desalting were obtained from Thermo Fisher Scientific, USA. Exact masses of the modified derivatives were determined by MALDI-TOF on ABISCIEX machine TripleTOF® 5600/5600. Urokinase was covalently immobilized onto cross-linked agarose (Sepharose 6B-CL) obtained from Pharmacia Ltd., Uppsala, Sweden. Chromogenic plasmin substrate, tosyl-Gly-Pro-Lys-anilide (Chromozyme® PL), was a product of Boehringer-Mannheim, USA. Plasmin inhibition kinetics was studied using commercially available $\alpha_2$-Antiplasmin from Calbiochem. All the reagents used were of the highest analytical grade available.

The present invention is described in further detail in the following non-limiting examples.

Example 1

Figure 2A:
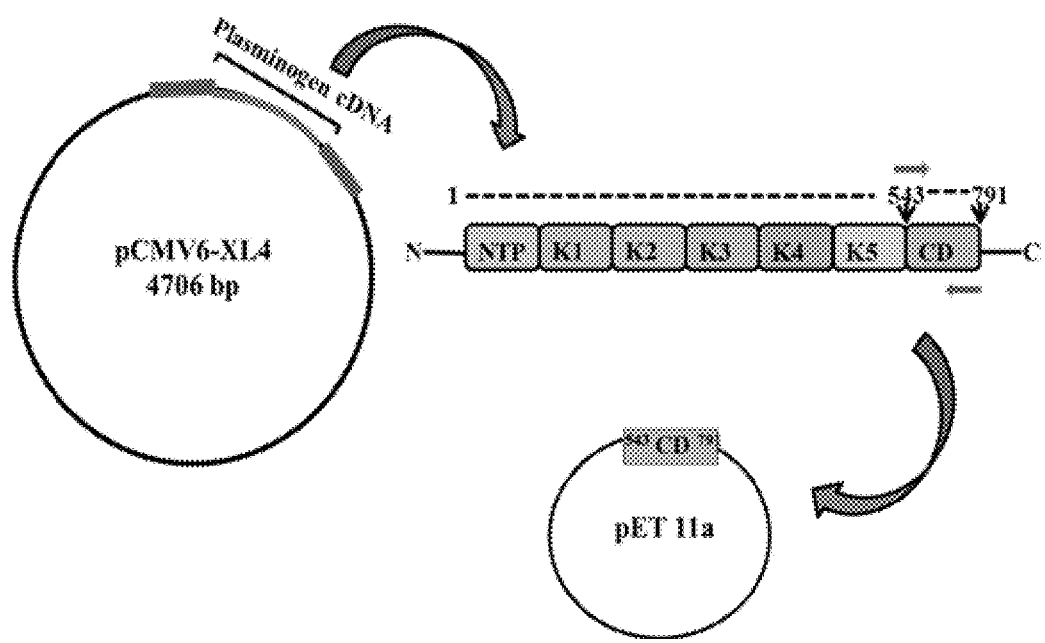
FIGS. 2A-2B: Cloning and mutagenesis of the catalytic domain of human plasminogen.

Cloning, Expression and Purification of Truncated Derivatives of Human Plasminogen The full length HPG cDNA (encoding protein having amino acid sequence as set forth in SEQ ID NO. 1) in pCMV6 vector was custom synthesized from Ori Gene Technologies Inc, USA. The nucleotide sequence coding for full length HPG available in NCBI (GenBank: AL109933.25) was used as a template for designing the forward and reverse primers for PCR amplification of the desired coding sequence. Overhang primers containing suitable restriction sites (Nde1/Hind III pair) for directional cloning in pET-11a were used for PCR amplification of micro-plasminogen. The amplified sequences restriction digested with Nde1/Hind III were then ligated into the pET-11a vector digested with the same set of restriction enzymes [FIG. 2a]. Sequence integrity of the clones was confirmed by nucleotide sequencing using Applied Biosystems 3130xl Genetic Analyser 16 capillary DNA sequencer. DNA constructs of micro-plasminogen (encoding amino acid sequence as set forth in SEQ ID NO. 2) were transformed into commercially BL-21 (DE3) cells for the heterologous expression under IPTG (isopropyl-thiogalactopyranoside) induced culture conditions. The protein was found to be expressed in the form of inclusion bodies, which were then solubilised in 8M urea and 10 mM DTT. The denatured and reduced protein was further subjected to in vitro refolding using refolding buffer (50 mM Tris-Cl pH 8.0, 1 mM EDTA, 1.6M urea, 20% glycerol, 1.25 mM GSH and 0.5 mM GSSG) for 2 days at 4° C. Refolded micro-plasminogen was purified by cation-exchange chromatography on SP-Sepharose column (GE-Amersham Biosciences).

Example 2

Design of PEGylation Sites

The selection of appropriate sites for surface modification is a critical step to maintain the functionality of the modified variants. The kringle-less derivative of plasminogen contains twelve cysteine residues, all of which are engaged in six disulphide linkages. Since none of intrinsic cysteines are free in natively folded micro-plasminogen, in vitro mutagenesis was used to strategically incorporate an unpaired cysteine into the micro-plasminogen which will be available for PEG-coupling. The technique of in vitro mutagenesis allows incorporation of a non-native, free cysteine residue into protein which can offer the benefit of selecting the target site for modification to obtain desired results without unwanted side effects.

The molecular surface of the catalytic domain of plasminogen consists of several distinct surface-exposed loops. The residues were selected on the basis of surface accessibility and association with $\alpha_2$-AP using available structural information. The docking models generated by GRAMM-X Protein-Protein Docking Web Server v.1.2.0 were analyzed using PyMOL graphic visualization system and used to interpret potential interface residues between these two proteins.

Five different locations consisting of two to eight residues were chosen by keeping it in mind that selected sites are distant from the catalytic site as well as the native cysteines of protein involved in disulfide linkage so that there is expected to be little interference with the fibrinolytic abilities [FIG. 1]. These sites include FGM (41-43); EKS (64-66); EVNLEPHV (81-88); GTF (148-150); AG (189-190) of SEQ ID NO: 2.

Example 3

Construction, Expressions and Purification of Mutants

Figure 2B:
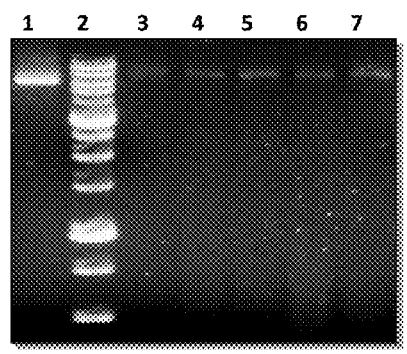
Figure 3:
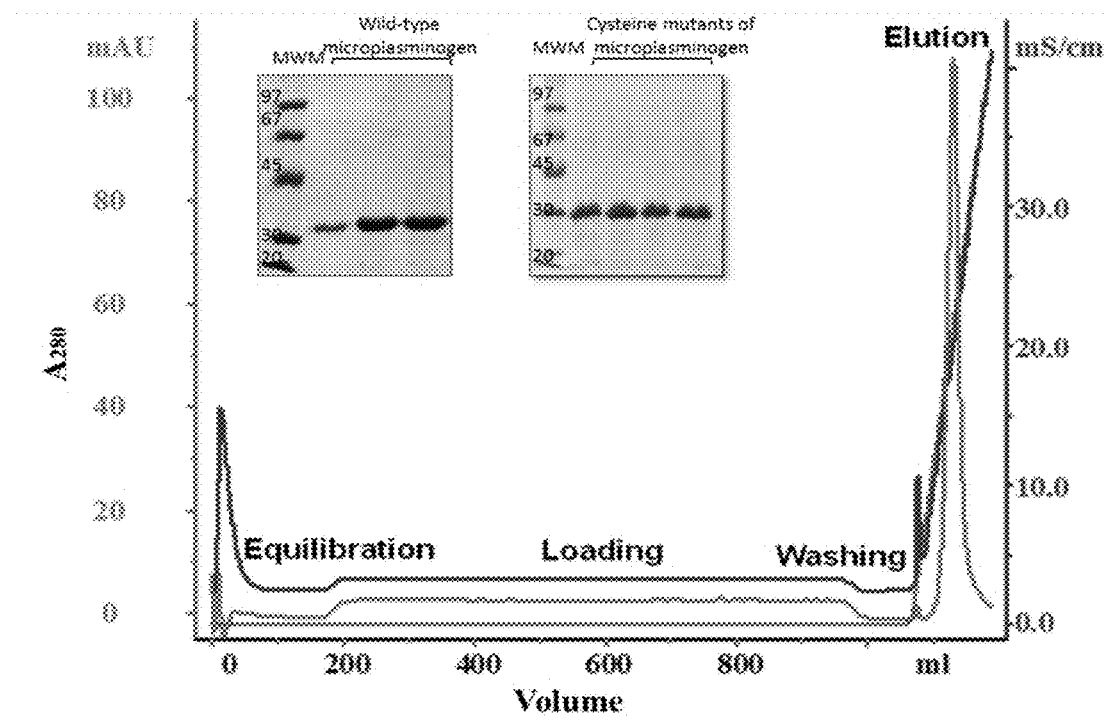
FIG. 3: Purification of wild-type micro-plasminogen as well cysteine variants of micro-plasminogen. Cation-exchange chromatography profile of the wild-type micro-plasminogen is shown here. Parameters such as absorbance at 280 nm, conductance and increase in concentration gradient have been represented with blue, green and red lines respectively. Similar chromatograms were obtained for the single and double cysteine variants. The SDS-PAGE pattern shown here confirms the purity of the eluted fractions of wild-type micro-plasminogen and its variants.

The variants of micro-plasminogen having cysteine mutations selected on the basis of computational studies are selected from the amino acid sequences as set forth in SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, and SEQ ID NO. 23. Variants of micro-plasminogen having single site substitution (SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 18, and SEQ ID NO. 20) as well as variants having double-site substitution (SEQ ID NO. 11, and SEQ ID NO. 12) were constructed based on the predicted locations using site-directed mutagenesis (QuickChange mutagenesis kit obtained from Stratagene Inc.) [FIG. 2b]. By the use of pfu turbo enzyme, both plasmid strands were replicated with high fidelity using two complementary primers having the desired mutation (listed in Table 2. named as SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, SEQ ID NO. 36, SEQ ID NO. 37, SEQ ID NO. 38, SEQ ID NO. 39, SEQ ID NO. 40, SEQ ID NO. 41, SEQ ID NO. 42, SEQ ID NO. 43). The parental plasmid was digested with DpnI enzyme that cleaves specifically the methylated and hemimethylated DNA. The plasmid was then transformed into *E. coli* XL1-Blue competent cells to obtain transformants which were further validated by DNA sequencing. All the variants were expressed as inclusion bodies, refolded and purified by cation-exchange chromatography by following the same methodology used for wild-type micro-plasminogen [FIG. 3]. Purified protein fractions were quantified using Bradford reagent.

TABLE 1

Single and double cysteine substitution on micro-plasminogen (AMINO ACID SEQUENCE IDs)

| MOLECULE (SEQ ID NOs) | MODIFICATION |
|---|---|
| SEQ ID 1. | HPG (Human Plasminogen) |
| SEQ ID 2. | HPG Catalytic Domain/Micro-plasminogen Cysteine Mutants |
| SEQ ID 3. | E81C Catalytic Domain |
| SEQ ID 4. | V82C Catalytic Domain |
| SEQ ID 5. | N83C Catalytic Domain |
| SEQ ID 6. | L84C Catalytic Domain |
| SEQ ID 7. | E85C Catalytic Domain |
| SEQ ID 8. | P86C Catalytic Domain |
| SEQ ID 9. | H87C Catalytic Domain |
| SEQ ID 10. | V88C Catalytic Domain |
| SEQ ID 11. | E85C-H87C Catalytic Domain |
| SEQ ID 12. | V82C-H87C Catalytic Domain |
| SEQ ID 13. | G148C Catalytic Domain |
| SEQ ID 14. | T149C Catalytic Domain |
| SEQ ID 15. | F150C Catalytic Domain |
| SEQ ID 16. | A189C Catalytic Domain |
| SEQ ID 17. | G190C Catalytic Domain |
| SEQ ID 18. | F41C Catalytic Domain |
| SEQ ID 19. | G42C Catalytic Domain |
| SEQ ID 20. | M43C Catalytic Domain |
| SEQ ID 21. | E64C Catalytic Domain |
| SEQ ID 22. | K65C Catalytic Domain |
| SEQ ID 23. | S66C Catalytic Domain |

TABLE 2

Primer sequence for cysteine substitution in Plasminogen catalytic domain/Micro-plasminogen

| S. No. | Name of Primer | Sequence ID | Sequence |
|---|---|---|---|
| 1. | E81C Catalytic Domain | SEQ ID 24 | Forward primer: GGTGCGCATCAATGTGTTAATCTCGAA |
| 2. | E81C Catalytic Domain | SEQ ID 25 | Reverse primer: TTCGAGATTAACACATTGATGCGCACC |
| 3. | V82C Catalytic Domain | SEQ ID 26 | Forward primer: CACACCAGGAATGCAATCTCGAACCG |
| 4. | V82C Catalytic Domain | SEQ ID 27 | Reverse primer: CGGTTCGAGATTGCATTCCTGGTGTG |
| 5. | N83C Catalytic Domain | SEQ ID 28 | Forward primer: ACCAGGAAGTGTGTCTCGAACCGCAT |
| 6. | N83C Catalytic Domain | SEQ ID 29 | Reverse primer: ATGCGGTTCGAGACACACTTCCTGGT |
| 7. | L84C Catalytic Domain | SEQ ID 30 | Forward primer: AAGAAGTGAATTGTGAACCGCATGTCCAG |
| 8. | L84C Catalytic Domain | SEQ ID 31 | Reverse primer: CTGGACATGCGGTTCACAATTCACTTCTT |
| 9. | E85C Catalytic Domain | SEQ ID 32 | Forward primer: AGTGAATCTTTGTCCGCATGTT |
| 10. | E85C Catalytic Domain | SEQ ID 33 | Reverse primer: AACATGCGGACAAAGATTCACT |
| 11. | P86C Catalytic Domain | SEQ ID 34 | Forward primer: AATCTCGAATGTCATGTCCAG |
| 12. | P86C Catalytic Domain | SEQ ID 35 | Reverse primer: CTGGACATGACATTCGAGATT |
| 13. | H87C Catalytic Domain | SEQ ID 36 | Forward primer: AATCTAGAACCGTGTGTGCAGGAA |
| 14. | H87C Catalytic Domain | SEQ ID 37 | Reverse primer: TTCCTGCACACACGGTTCTAGATT |
| 15. | V88C Catalytic Domain | SEQ ID 38 | Forward primer: CGAACCGCATTGTCAGGAGATAGAA |

TABLE 2-continued

Primer sequence for cysteine substitution in Plasminogen catalytic domain/Micro-plasminogen

| S. No. | Name of Primer | Sequence ID | Sequence |
|---|---|---|---|
| 16. | V88C Catalytic Domain | SEQ ID 39 | Reverse primer: TTCTATCTCCTGACAATGCGGTTCG |
| 17. | F41C Catalytic Domain | SEQ ID 40 | Forward primer: AGAACTAGGTGTGGAATGCAT |
| 18. | F41C Catalytic Domain | SEQ ID 41 | Reverse primer: ATGCATTCCACACCTAGTTCT |
| 19. | M43C Catalytic Domain | SEQ ID 42 | Forward primer: AGGTTTGGATGTCACTTCTGT |
| 20. | M43C Catalytic Domain | SEQ ID 43 | Reverse primer: ACAGAAGTGACATCCAAACCT |

Example 4

Quantitation of Thiols and PEGylation Reaction

The number of free thiols in cysteine variant proteins was measured by a classical colorimetric method using Ellman's reagent 5,5'-dithiobis (2-nitrobenzoic acid). DTNB or 5,5'-dithiobis (2-nitrobenzoic acid) reacts with thiol groups to form a mixed disulphide of the protein and one mole of 2-nitro 5 thiobenzoate per mole of protein sulphydryl group. The amount and concentration of free sulphydryls per molar concentration of protein sample is calculated from the molar extinction coefficient of TNB dianions and the absorbance value of protein at 412 nm. β-mercaptoethanol having single free thiol was used standard.

Figure 4:
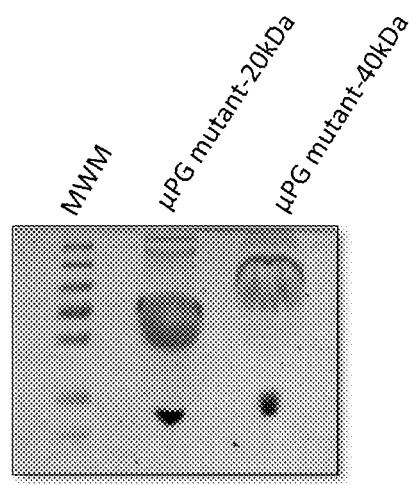
FIG. 4: Crude PEGylation reaction. 12% SDS-PAGE profile confirms the coupling of PEG groups (20 kDa and 40 kDa) to cysteine variant of micro-plasminogen. In both cases, PEGylation reaction yielded near-homogeneous covalently modified micro-plasminogen variants. It was observed that mono-PEG as well as bi-PEG variants tend to migrate at a higher apparent molecular weight than the one predicted from the sum of the molecular weights of both protein and PEG group.

Following the validation of present free thiol groups, the proteins were then incubated with 15-20 fold molar excess of maleimide-activated linear methoxy PEG (JenKem Technology USA) of different molecular weight (eg. 20 kDa, 40 kDa) in presence of 100 mM Tris-Cl (pH 8) and 2 mM EDTA. The reaction mixture was allowed to gently stir for 3 h at room temperature. [FIG. 4] The reaction mix was desalted with 20 mM sodium acetate, pH 5.5 using Zeba™ Spin desalting columns (Thermo Fisher Scientific Inc. USA).

Example 5

Purification and Activation of PEGylated Proteins

Figure 5A:
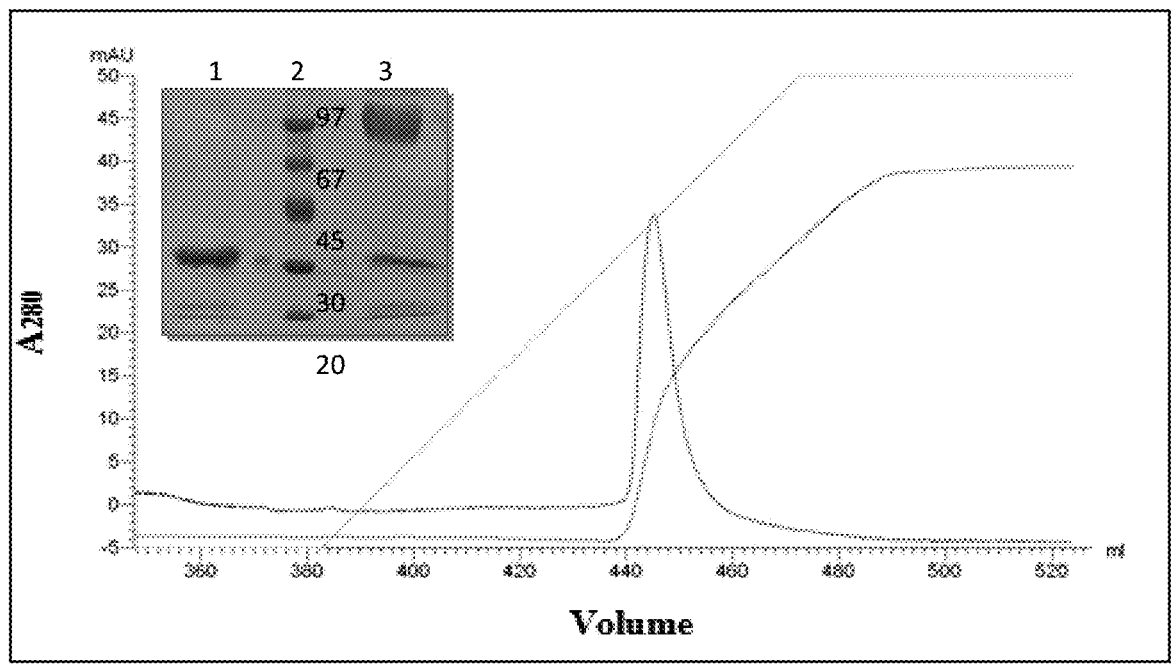
FIGS. 5A and 5B Purification of PEGylated micro-plasminogen variants.
Figure 5B:
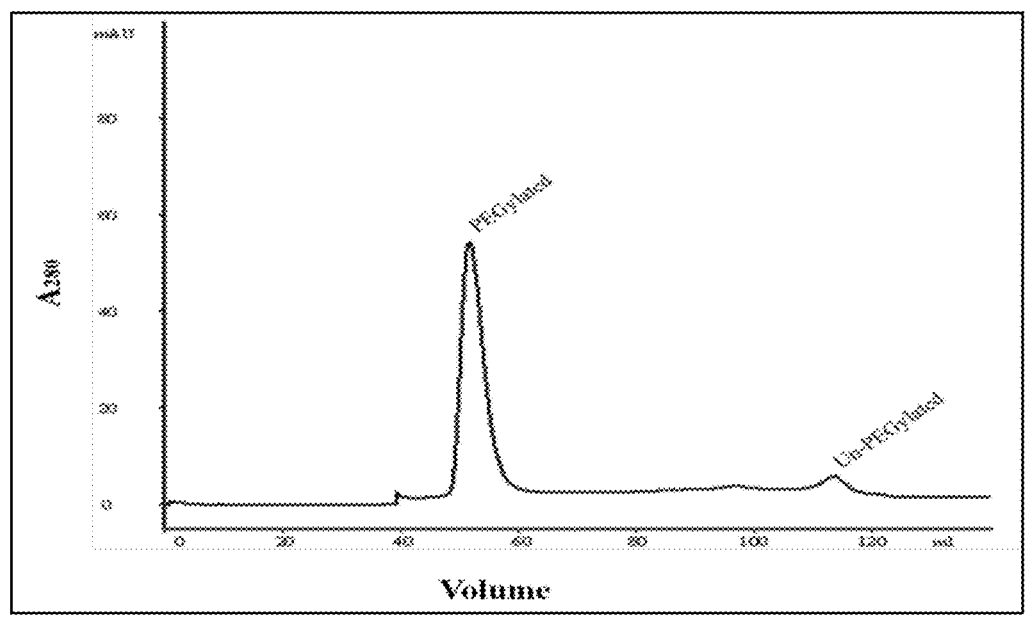
Figure 6A:
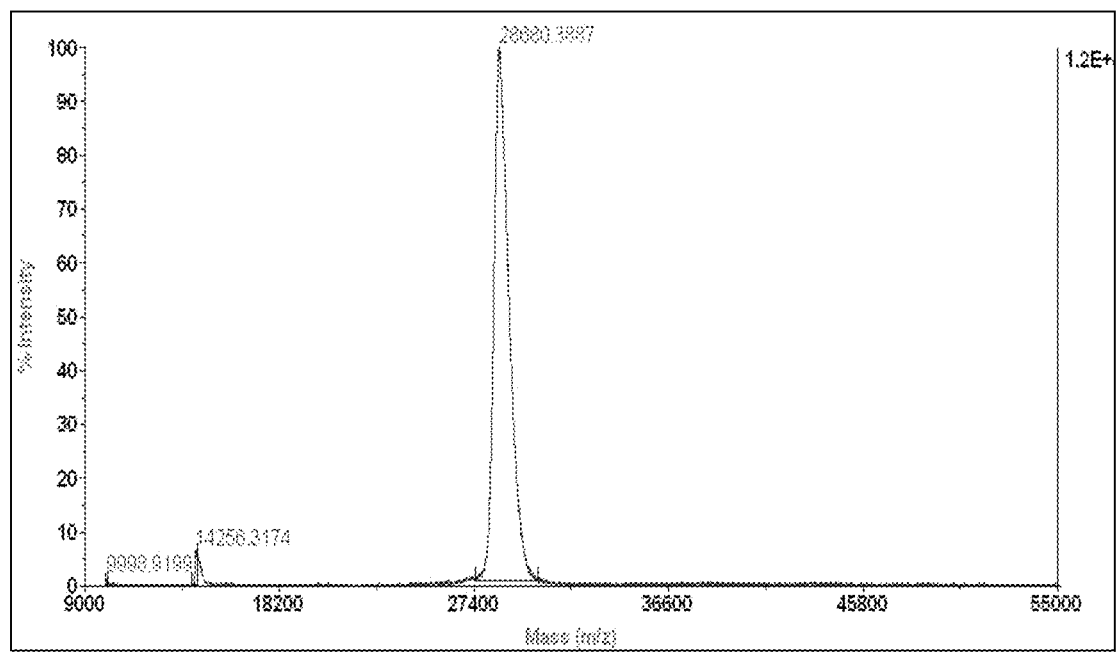
FIGS. 6A-6D: Mass analysis of the micro-plasminogen and its PEGylated variants. MALDI-TOF data of the µPG and PEGylated variants confirmed their size, which were close to the expected ones. Expected masses of proteins are shown for wild-type µPG ~28 kDa (FIG. 6A); µPG cysteine variant (FIG. 6B); mono-PEGylated µPG variant ~48 kDa (FIG. 6C); and bi-PEGylated µPG variant ~68 kDa (FIG. 6D).
Figure 6B:
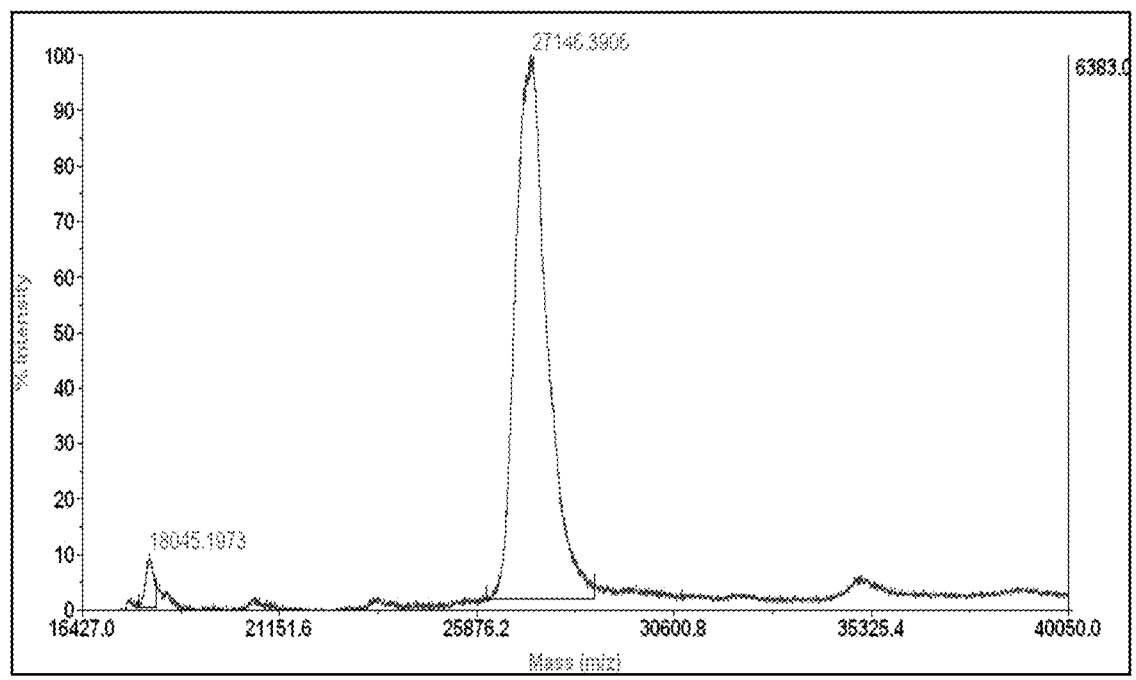
Figure 6C:
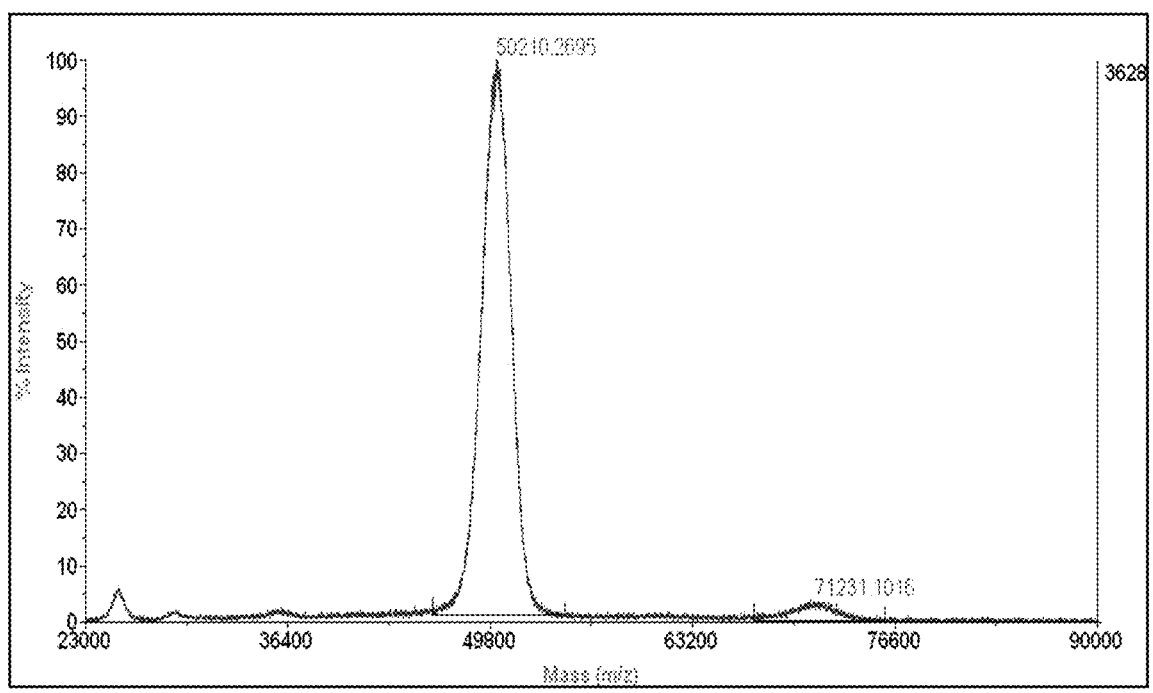
Figure 6D:
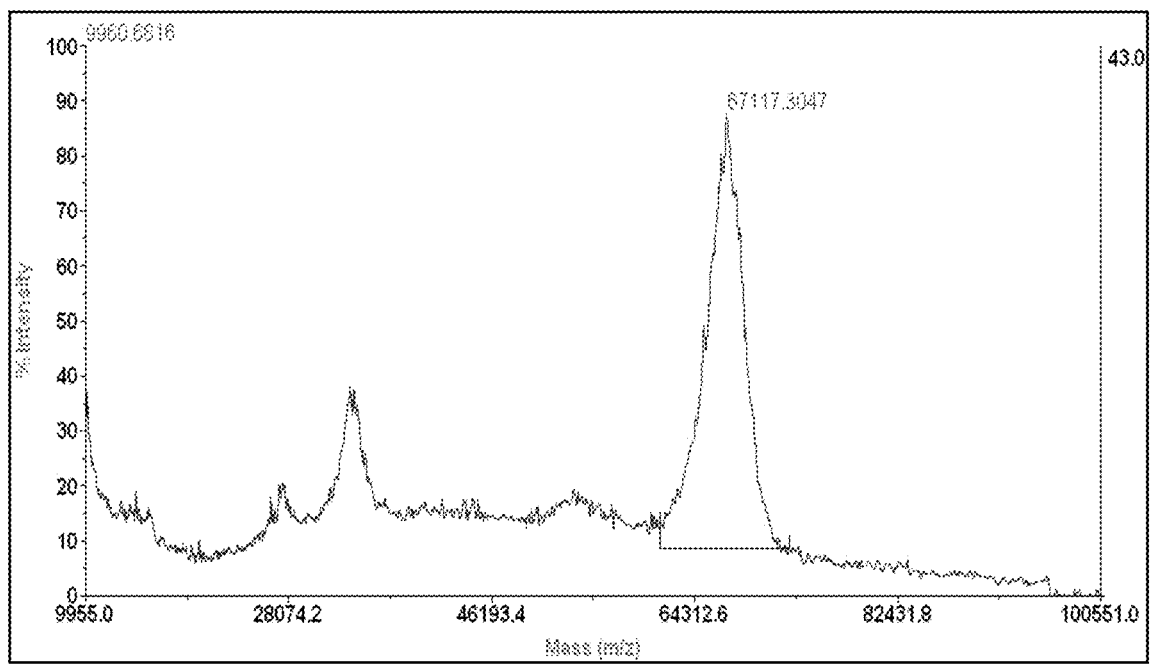

Desalted PEGylation reaction mixture (consisting of PEG-protein conjugate, un-reacted protein and polymer, described in example 4) was diluted 10 times with 20 mM sodium acetate, pH 5.5 and loaded onto a SP-Sepharose column (GE Healthcare life sciences) pre-equilibrated in 20 mM sodium acetate, pH 5.5. After washing with 2-3 bed volumes of 20 mM sodium acetate, pH 5.5, bound protein was eluted using linear gradient of 1M NaCl. The eluted protein fraction was further purified to obtain more uniform PEGylated product using Superdex-75 pg (16×600 mm) (GE Healthcare Life Sciences, USA) size exclusion chromatography to separate un-reacted protein fraction from the PEGylated protein [FIG. 5]. All the purifications were performed using AKTA purifier system (GE Healthcare Life Sciences, USA). Quantitative amino acid composition analysis of PEGylated variants was performed using a Waters® Pico-Tag HPLC Amino Acid Analysis System.

The purified mono-PEGylated as well as bi-PEGylated thiol derivatives of micro-plasminogen were converted to their active forms (microplasmin) using urokinase-coupled sepharose beads in presence of 50 mM Tris-Cl (pH 8), 25 mM lysine and 25% glycerol. The reaction was set up at 25° C. with slow stirring from for upto 8 hours and monitored at regular intervals using Chromozym® PL.

Example 6

Characterization of PEGylated and Un-PEGylated Micro-Plasminogen Variants

PEGylated micro-plasminogen variants (SEQ ID NO. 3; SEQ ID NO. 4, SEQ ID NO. 5, SEQ ID NO. 6, SEQ ID NO. 7, SEQ ID NO. 8, SEQ ID NO. 9. SEQ ID NO. 10, SEQ ID NO. 11, SEQ ID NO. 12, SEQ ID NO. 18, SEQ ID NO. 20) as well as un-PEGylated micro-plasminogen (SEQ ID NO. 2) were further characterized. All the variants were checked for their purity on the SDS-PAGE. The protein sample was mixed in 5× loading reducing dye and separated on 12% polyacrylamide gel. Furthermore, the accurate molecular weights of both PEGylated as well un-PEGylated derivatives were determined by MALDI-TOF on ABISCIEX machine TripleTOF® 5600/5600 [FIG. 6]. CD analysis was performed to investigate the secondary structure of micro-plasminogen variant upon PEGylation. Far-UV CD spectra of wild-type micro-plasminogen as well as their PEGylated variants (concentration ~0.25 mg/ml in phosphate-buffer saline, pH 7.2) were recorded from 195-250 nm on Jasco J-815 spectropolarimeter using cuvette of path length 0.1 cm. Both the PEGylated variant as well as wild-type micro-plasminogen exhibited similar secondary structure content, indicating that secondary structure is essentially not influenced by PEGylation. The hydrodynamic radii of micro-plasminogen analogs were determined by dynamic light scattering (DLS). The data suggested that attachment of PEG moieties has significantly expanded the hydrodynamic radii of the protein sample [Table 3].

TABLE 3

Hydrodynamic size measurement (DLS)

| Construct | $R_h$, Average Hydrodynamic radius (nm) |
|---|---|
| Micro-plasminogen (μPG) (SEQ ID NO. 2) | 2.6 |

TABLE 3-continued

Hydrodynamic size measurement (DLS)

| Construct | $R_h$, Average Hydrodynamic radius (nm) |
|---|---|
| Mono-PEGylated µPG variants (20 kDa) (SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 18, SEQ ID NO. 20) | 5.8 |
| Mono-PEGylated µPG variants (40 kDa) (SEQ ID NO. 4, SEQ ID NO. 7, SEQ ID NO. 9) | 6.4 |
| Bi-PEGylated µPG variants (20 kDa-20 kDa) (SEQ ID NO. 11, SEQ ID NO. 12) | 4.7 |

Example 7

Evaluation of Activity of PEGylated Micro-Plasmin Variants

The PEGylated variants (SEQ ID NO. 4, SEQ ID NO. 7, SEQ ID NO. 8, SEQ ID NO. 9, SEQ ID NO. 10, SEQ ID NO. 11, SEQ ID NO. 12) were assessed for amidolytic as well α₂-AP inhibition activity.

The enzymatic activity of PEGylated-microplasmin variants were monitored with the substrate, Chromozym® PL (0.5 mM), at 37° C. in presence of 50 mM Tris-Cl, pH 7.4, 0.1 M NaCl and 0.5% BSA. Absorbance was recorded at 405 nm for 10 minutes. Enzyme activities of the all cysteine variants and their PEGylated forms were compared to that of wild type micro-plasmin [Table 4]. The results show that there amidolytic parameters were not substantially affected upon PEGylation, however, a slight increase in Michaelis-Menten constant (Km) values can be accounted for slightly reduced accessibility.

TABLE 4

Amidolytic parameters of wild-type and PEGylated micro-plasmin(ogen) variants

Figure 7A:
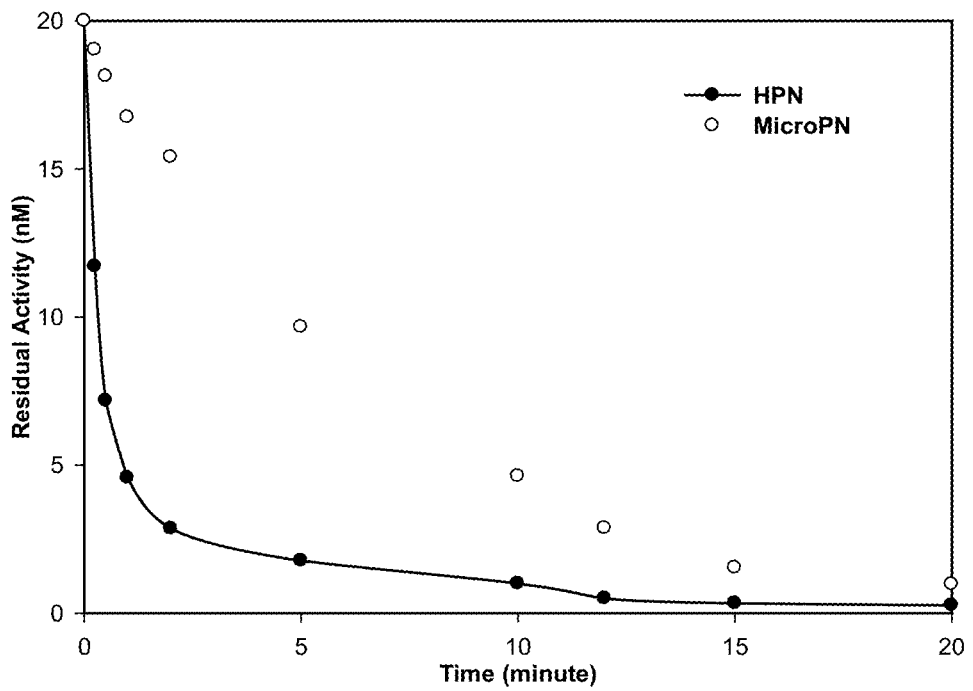
FIGS. 7A-7C: Time dependent inhibition of wild-type micro-plasmin and PEGylated variants by $\alpha_2$-antiplasmin.
Figure 7B:
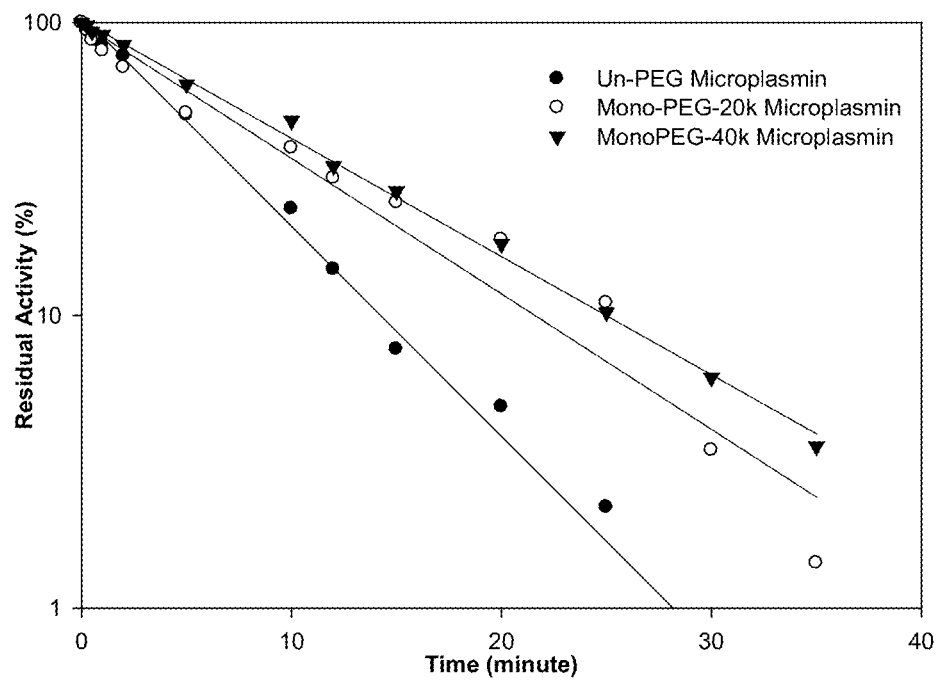
Figure 7C:
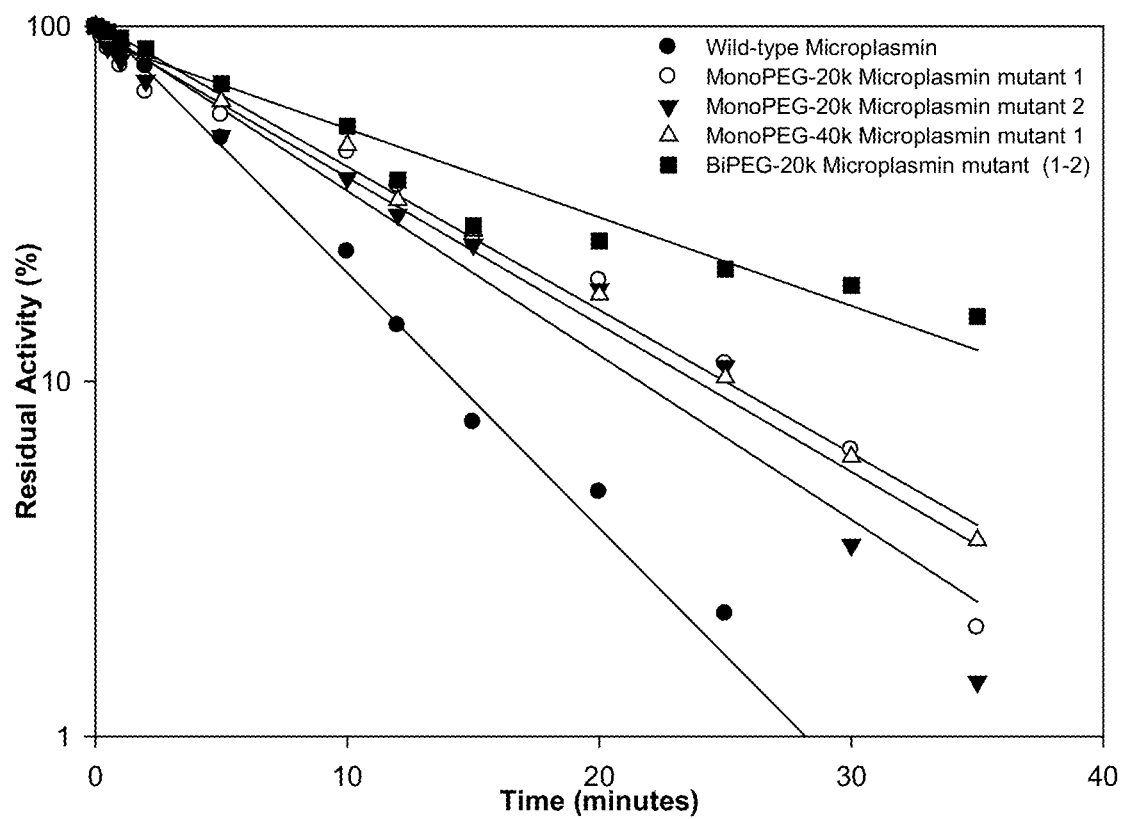

| | Amidolytic Parameters | | |
|---|---|---|---|
| Construct | Km µM | Kcat s⁻¹ | kcat/Km µM⁻¹ s⁻¹ |
| Microplasminogen (µPG) (SEQ ID NO. 2) | 2013 ± 201 | 18 ± 0.8 | 0.008 |
| Mono-PEGylated µPG variants (20 kDa) (SEQ ID NO. 4, SEQ ID NO. 7, SEQ ID NO. 8, SEQ ID NO. 9, SEQ ID NO. 10) | 2290 ± 254 | 23.45 ± 2.5 | 0.010 |
| Mono-PEGylated µPG variants (40 kDa) (SEQ ID NO. 4, SEQ ID NO. 7, SEQ ID NO. 8, SEQ ID NO. 9, SEQ ID NO. 10) | 2519 ± 430 | 26.05 ± 2.5 | 0.010 |
| Bi-PEGylated µPG variants (20 kDa-20 kDa) (SEQ ID NO. 11, SEQ ID NO. 12) | 2310 ± 220 | 21.32 ± 4.5 | 0.009 |

α₂-AP inhibition kinetics was performed by separately adding PEGylated micro-plasmin variants (20 nM) and antiplasmin (60 nM) to cuvette containing 100 mM sodium phosphate, pH 7.2 and incubating at 25° C. for the time interval ranging 15 sec-30 minutes. Change in absorbance at 405 nm was recorded at 60 s intervals after the addition of 0.5 mM Chromozym® PL. The residual enzyme activity was measured at different intervals from the slope of the curve and plotted as log % residual activity versus time (Wiman et al., 1978; Turner et al., 2002) as shown in FIG. 7, which display a representative data demonstrating the effect of PEGylation on α₂-AP mediated inhibition kinetics of microplasmin mutants designed on the basis of interaction site prediction by docking analysis of microplasmin(ogen) and α₂-AP. PEGylated microplasmin analogues could retain their activity for longer as compared to their un-Pegylated counterparts [Table 5]. The data shown here in Table 5 represents the average values. This transient resistant behavior of PEGylated microplasmin derivatives may be ascribed to the properties of steric interference caused by PEG moiety at critical protein-protein contacts, resulting in a slower complexation between the two proteins. Interestingly, the inhibition of mutants by α₂-AP is not irreversible, but apparently only a kinetic one since after the delay, full native-like inhibition is seen. Herein, site-specific PEG-conjugation of microplasmin has been observed to minimize/modulate substrate-inhibitor/protein-protein intermolecular interactions, without abolishing them completely. Similar effects of PEGylation are expected in other site specific microplasmin variants (described in EXAMPLE 2) designed with the help of docking analysis.

TABLE 5

In vitro half-life of inactivation of PEGylated and unmodified Plasmin(ogen) variants by α₂-antiplasmin

| S. NO. | Plasmin(ogen) variant | In vitro Half-life |
|---|---|---|
| 1. | Wild-type Micro-plasmin (SEQ ID NO. 2) | >5 min |
| 2. | Mono-PEGylated Micro-plasmin variant (20 kDa PEG) (SEQ ID NO. 4, SEQ ID NO. 7, SEQ ID NO. 8, SEQ ID NO. 9, SEQ ID NO. 10) | 6-7 min |
| 3. | Mono-PEGylated Micro-plasmin variant (40 kDa PEG) (SEQ ID NO. 4, SEQ ID NO. 7, SEQ ID NO. 8, SEQ ID NO. 9, SEQ ID NO. 10) | >7 min |
| 4. | Bi-PEGylated Micro-plasmin variant (20 kDa-20 kDa PEG) (SEQ ID NO. 11, SEQ ID NO. 12) | >10 min |

Advantages of the Invention

The present invention provides a method that can be utilized for designing of highly potent, longer-acting plasmin derivatives. Covalently modified plasmin variants capable of significantly retarding antiplasmin-mediated inhibition, offers an advantage of enhanced half-life thereby, making it "therapeutically effective" as compared to the unmodified plasmin and derivatives thereof.

The composition comprising strategically designed PEGylated variants of micro-plasminogen possessing dual properties of delayed inhibition (evasion of inactivation) by endogenous $\alpha_2$-antiplasmin along with its intrinsic fibrinolytic ability would be beneficial for the treatment of various thrombotic disorders such as pulmonary embolism, myocardial infarction, or ischemic stroke. Furthermore, the retention of micro-plasmin activity for longer period by delaying the course of interaction with $\alpha_2$-AP inhibitor by appropriate placement of PEG groups would facilitate developing the conjugates as lower dose formulation/s. Moreover, the slow inhibitory reaction of micro-plasmin upon site-specific conjugation of a flexible PEG group, instead of a more rigid moiety or other disruptive mutation, would tend to prevent the undesired consequence of permanent inhibition of $\alpha_2$-AP, thereby maintaining the safety of micro-plasmin derivative molecules in thrombolytic therapy.

To improve thrombolytic therapy, it is necessary to increase the rate and extent of clot lysis without inducing a systemic lytic state. These novel PEGylated micro-plasmin variants are expected to be attractive candidates for thrombolytics possessing controllable/tunable half-life.

REFERENCES

1. Adivitiya, Khasa Y P (2017). The evolution of recombinant thrombolytics: Current status and future directions. Bioengineered 4; 8(4):331-358.
2. Ambrus J L, Ambrus C M, Bock N et al. (1957). Clinical and experimental studies on fibrinolytic enzymes. Ann New York AcadSci 68: 97.
3. Aoki N (2005). Discovery of alpha2-plasmin inhibitor and its congenital deficiency. J ThrombHaemost; 3:623-631.
4. Bailon P, Berthold W (1998) Polyethylene glycol-conjugated pharmaceutical proteins. Pharm SciTechnolo 1: 352-356.
5. Boyles P W, Meyer W H, Graff J, Ashley C C, Ripic R C (1960). Comparative effectiveness of intravenous and intra-arterial fibrinolysis therapy. In: Clifton E C, ed. Symposiumon Fibrinolysis. Am J Cardiol 6:539-46.
6. Cazalis C S, Haller C A, Sease-Cargo L, Chaikof E L (2004) C-Terminal site-specific PEGylation of a truncated thrombomodulin mutant with retention of full bioactivity. BioconjugChem 15: 1005-1009.
7. Chapman A P (2002) PEGylated antibodies and antibody fragments for improved therapy: a review. Adv Drug Deliv Rev 54:531-545.
8. Chapman A P, Antoniw P, Spitali M, West S, Stephens S, and King D J (1999). Therapeutic antibody fragments with prolonged in vivo half-lives. Nat Biotechnol 17:780-783.
9. Chen W, Huang X, Ma X W, Mo W, Wang W J, Song H Y (2008). Enzymatic vitreolysis with recombinant microplasminogen and tissue plasminogen activator. Eye (Lond) 22:300-307
10. Chiu K, Agoubi L L, Lee I, Limpar M T, Lowe J W, et al. (2010) Effects of polymer molecular weight on the size, activity, and stability of PEG functionalized trypsin. Biomacromolecules 11: 3688-3692.
11. Clifton E E (1957). The use of plasmin in humans Ann New York AcadSci 68: 209-29.
12. Cohen D, Lijnen H R (1991). Basic and clinical aspects of fibrinolysis and thrombolysis. Blood 78:3114.
13. Cohen D (1985). The Main Components of the Fibrinolytic System: Biochemical and Physiological Properties. European Heart Journal, 6; 193-195
14. Cohen, D, Sinnaeve, P, Demarsin, E, Moreau, H, De Maeyer, M, Jespers, L, Laroche, Y, and Van de Werf, F (2000). Polyethylene glycol-derivatized cysteine-substitution variants of recombinant staphylokinase for single-bolus treatment of acute myocardial infarction. Circulation 102(15): 1766-72
15. Crumrine R C, Marder V J, Taylor G M, et al. (2012). Safety evaluation of a recombinant plasmin derivative lacking kringles 2-5 and rt-PA in a rat model of transient ischemic stroke. Experimental & Translational Stroke Medicine 4:10.
16. De Smet M D, Valmaggia C, Zarranz-Ventura J, Willekens B (2009). Microplasmin: ex vivo characterization of its activity in porcine vitreous. Invest Ophthalmol Vis Sci 50(2):814-9.
17. Doherty D H, Rosendahl M S, Smith D J, Hughes J M, Chlipala E A, Cox G N (2005). Site-specific PEGylation of engineered cysteine analogues of recombinant human granulocyte-macrophage colony-stimulating factor. Bioconjug Chem. 16(5):1291-1298
18. Fishburn C S (2008). The pharmacology of PEGylation: Balancing PD with PK to generate novel therapeutics. J Pharm Sci. 97: 4167-4183.
19. Gaberc-Porekar V, Zore I, Podobnik B, Menart V (2008). Obstacles and pitfalls in the PEGylation of therapeutic proteins. Curr. Opin. Drug Discov. Dev. 11:242-250
20. Grace M, Lee S, Bradshaw S, Chapman J, Spond J, Cox S, Delorenzo M, Brassard D, Wylie D, Cannon-Carlson S, Ccullen, Indelicato S, Voloch M, and Bordens R. (2005) Site of pegylation and polyethylene glycol molecule size attenuate interferon-$\alpha$ antiviral and antiproliferative activities through the JAK/STAT signaling pathway. J. Biol. Chem. 280 (8), 6327-6336.
21. Greenwald R B, Choe Y H, McGuire J, Conover C D (2003) Effective drug delivery by PEGylated drug conjugates. Adv Drug Deliv Rev 55: 217-250.
22. Hamed E, Xu, T, Keten S (2013). Poly(Ethylene Glycol) Conjugation Stabilizes the Secondary Structure of A-Helices by Reducing Peptide Solvent Accessible Surface Area. Biomacromolecules 14, 4053-4060.
23. Hao Y, Chen J, Wang X, Zhu H, Rong Z (2006). Effects of site-specific polyethylene glycol modification of recombinant human granulocyte colony-stimulating factor on its biologic activities. BioDrugs 20: 357-362.
24. Harris J M and Chess R B (2003) Effect of pegylation on pharmaceuticals. Nat Rev Drug Discov 2:214-221.
25. Harris J M and Veronese F M (2003). "Peptide and Protein pegylation II—clinical evaluation", Ad. Drug Del. Rev. 55: 1259-1350.
26. Hunt J A, Petteway S R Jr, Scuderi P, Novokhatny V (2008). Simplified recombinant plasmin: production and functional comparison of a novel thrombolytic molecule with plasma-derived plasmin ThrombHaemost 100(3): 413-9.
27. Jensen V J (1976). U.S. Pat. No. 3,950,513. Process of stabilizing therapeutically useful plasmin solutions. Novo TerapeutiskLaboratorium (assignee).
28. King D J, Turner A, Farnsworth A P, Adair J R, Owens R J, Pedley R B, Baldock D, Proudfoot K A, Lawson A D, Beeley N R, et al. (1994) Improved tumor targeting with chemically cross-linked recombinant antibody fragments. Cancer Res 54:6176-6185.
29. Kurfurst, M M (1992). Detection and molecular weight determination of polyethylene glycol-modifedhirudin by staining after sodium dodecyl sulfate-polyacrylamide gel electrophoresis. Anal Biochem 200, 244-248
30. Lapchak P A, Araujo D M, Pakola S, Song D, Wei J, Zivin J A (2002). Microplasmin: a novel thrombolytic that improves behavioral outcome after embolic strokes in rabbits. Stroke. 33: 2279-2284.
31. Law, R H P, Sofian, T, Kan, W T, Horvath, A J, Hitchen, C R, Langendorf, C G, Buckle, A M, Whisstock, J C, Coughlin, P B (2008). X-ray crystal structure of the fibrinolysis inhibitor {alpha}2-antiplasmin. Blood 111: 2049-2052.
32. Marder V J, Landskroner K, Novokhatny V, Zimmerman T P, Kong M, Kanouse J J, Jesmok G (2001). Plasmin induces local thrombolysis without causing hemorrhage: a comparison with tissue plasminogen activator in the rabbit. ThrombHaemost 86: 739-45.
33. Marder V J (2011). Historical perspective and future direction of thrombolysis research: the re-discovery of plasmin. J ThrombHaemost; 9 (Suppl 1):364-73.
34. Meng, W, Guo X, Qin M, Pan H, Cao Y, Wang W (2012). Mechanistic Insights into the Stabilization of Srcsh3 by Pegylation. Langmuir, 28, 16133-16140.
35. Milla P, Dosio F, Cattel L (2012) PEGylation of Proteins and Liposomes: a Powerful and Flexible Strategy to Improve the Drug Delivery. Curr Drug Metab 13: 105-119.
36. Mok, H, Palmer D J, Ng P, Barry M A (2005). Evaluation of polyethylene glycol modification of first-generation and helper-dependent adenoviral vectors to reduce innate immune responses. Mol. Ther. 11, 66-79.
37. Nagai N, De Mol M, Lijnen H R, Carmeliet P, Collen D (1999). Role of plasminogen system components in focal cerebral ischemic infarction: a gene targeting and gene transfer study in mice. Circulation. 99: 2440-2444.
38. Nagai N, De Mol M, Van Hoef B, Verstreken M, Collen D (2001). Depletion of circulating $\alpha_2$-antiplasmin by intravenous plasmin or immunoneutralization reduces focal cerebral ischemic injury in the absence of arterial recanalization. Blood 97: 3086-92.
39. Nagai N, Demarsin E, Van Hoef B, Wouters S, Cingolani D, Laroche Y, Collen D (2003). Recombinant human microplasmin: production and potential therapeutic properties. J Thromb Haemost.1 (2): 307-313.
40. Novokhatny V (2008). Structure and activity of plasmin and other direct thrombolytic agents. Thromb Res. 122 (Suppl 3):S3-S8.
41. Ozbakir H F and Scott Banta (2018). Kinetic and Transport Effects on Enzymatic Biocatalysis Resulting from the PEGylation of Cofactors A IChE Journal 64 (1)
42. Pakola S, Cahillane G, Stassen J M, Lijnen H R, Verhamme P (2009). Neutralization of alpha(2)-antiplasmin by microplasmin: a randomized, double-blind, placebo-controlled, ascending-dose study in healthy male volunteers. ClinTher. 31:1688-1706

43. Pandey B K, Smith M S, Torgerson C, Lawrence P B, Matthews S S, Watkins E, Groves M L, Prigozhin, M B, Price J L (2013) Impact of Site-Specific Pegylation on the Conformational Stability and Folding Rate of the Pin Ww Domain Depends Strongly on Peg Oligomer Length. Bioconjugate Chem. 24, 796-802.
44. Petersen T E, Martzen M R, Ichinose A, and Davie E W (1990). Characterization of the gene for human plasminogen, a key proenzyme in the fibrinolytic system. J. Biol. Chem. 265:6104-6111.
45. Qimeng Mu, Tao Hu, Jingkai Yu (2013). Molecular Insight into the Steric Shielding Effect of PEG on the Conjugated Staphylokinase: Biochemical Characterization and Molecular Dynamics Simulation. PLoS ONE 8(7).
46. Reed G L, Houng A K, Wang D (2014). Microvascular thrombosis, fibrinolysis ischemic injury, and death after cerebral thromboembolism are affected by levels of circulating $\alpha_2$-antiplasmin ArteriosclerThrombVasc Bio134: 2586-2593.
47. Reed G L, Matsueda G R, and Haber E (1990.). Inhibition of Clot-Bound $\alpha_2$-Antiplasmin Enhances In Vivo Thrombolysis. Circulation 82(1):164-168.
48. Reed G L (2004) Compositions and methods for treating thrombotic treatments. WO 2004/045558 A2.
49. Reed G L (1997). Functional characterization of monoclonal antibody inhibitors of alpha 2-antiplasmin that accelerate fibrinolysis in different animal plasmas. Hybridoma. 16(3):281-6.
50. Robbins K C, Summaria L, Hsieh B, Shah R J (1967). The peptide chains of human plasmin. Mechanism of activation of human plasminogen to plasmin. J Biol Chem. 242: 2333-42.
51. Roberts M J, Bentley M D. Harris J M (2002). Chemistry for peptide and protein PEGylation. Adv. Drug Deliv. Rev. 54, 459-476.
52. Sakata Y, Aoki N (1982). Significance of cross-linking of $\alpha_2$-plasmin inhibitor to fibrin in inhibition of fibrinolysis and in hemostasis. J Clin Invest. 69:536-542.
53. Singh S, Houng A, Reed G L (2017). Releasing the brakes on the fibrinolytic system in pulmonary emboli: unique effects of plasminogen activation and $\alpha_2$-antiplasmin inactivation. Circulation. 135:1011-1020.
54. Suzuki Y, Chen F, Ni Y, Marchal G, Collen D, Nagai N (2004). Microplasmin reduces ischemic brain damage and improves neurological function in a rat stroke model monitored with MRI. Stroke. 35:2402-2406.
55. Thijs, V N, Peeters A, Vosko M, Aichner F and Schellinger P D et al., (2009). Randomized, placebo-controlled, dose-ranging clinical trial of intravenous microplasmin in patients with acute ischemic stroke, 40: 3789-3795.
56. Tovchigrechko A, Vakser I A (2006). GRAMM-X public web server for protein-protein docking. Nucleic Acids Res. 34:W310-4.
57. Turner R B, Liu L, Sazonova I Y, Reed G L (2002). Structural elements that govern the substrate specificity of the clot dissolving enzyme plasmin. J Biol Chem. 277: 33068-74.
58. US FDA (2016). Jetrea® safety and utilization review.
59. Veronese F M (2001). Peptide and Protein P EGylation: a review of problems and solutions, Biomaterials, 22; 405-417.
60. Wang X, Terzyan S, Tang J, Loy J A, Lin X, Zhang X C (2000). Human plasminogen catalytic domain undergoes an unusual conformational change upon activation J. Mol. Biol. 295: 903-914.

61. Weir A N, Nesbitt A, Chapman A P, Popplewell A G, Antoniw P, and Lawson A D. (2002) Formatting antibody fragments to mediate specific therapeutic functions. BiochemSoc Trans 30:512-516.
62. Wiman B, Boman L, and Collen D (1978). On the Kinetics of the Reaction between Human Antiplasmin and a Low-Molecular-Weight Form of Plasmin Eur. J. Biochem. 87, 143-146.
63. Wiman B, Caen D (1979). On the mechanism of the reaction between human alpha 2-antiplasmin and plasmin. J Biol Chem. 254(18):9291-9297.
64. Wiman B, Lijnen H R, Cohen D (1979). On the specific interaction between the lysine-binding sites in plasmin and complementary sites in alpha 2-antiplasmin and in fibrinogen. BiochimBiophysActa 579: 142-54.
65. Yang K, Basu A, Wang M, Chintala R, Hsieh M C, Liu S, Hua J, Zhang Z, Zhou J, Li M, et al. (2003). Tailoring structure-function and pharmacokinetic properties of single-chain Fv proteins by site-specific PEGylation. Protein Eng 16:761-770.
66. Zheng J C, Lei N, He Q C, Hu W, Jin J G, et al. (2012). PEGylation is effective in reducing immunogenicity, immunotoxicity, and hepatotoxicity of alpha momorcharin in vivo. ImmunopharmacolImmunotoxicol 34: 866-873.

We claim:

1. A fibrinolytic composition comprising:
   (a) a thiol derivative of plasminogen comprising a substitution of one to eight amino acid residues in a catalytic domain of SEQ ID NO: 2 with a cysteine residue, wherein the thiol derivative of plasminogen comprises an amino acid sequence selected from SEQ ID NOs: 3-23 and a polyethylene glycol (PEG) moiety covalently-bound to the cysteine residue; and
   (b) a pharmaceutically acceptable diluent, carrier, or adjuvant.

2. The fibrinolytic composition of claim 1, wherein the catalytic domain comprises the sequence EVNLEPHV (amino acids 81-88 of SEQ ID NO: 2), wherein the substitution is selected from the group consisting of E81C, V82C, N83C, L84C, E85C, P86C, H87C, V88C, E85C-H87C, and V82C-H87C, and wherein the thiol derivative of plasminogen comprises an amino acid sequence selected from SEQ ID NOs: 3-12.

3. The fibrinolytic composition of claim 1, wherein the catalytic domain comprises the sequence GTF, wherein the substitution is selected from the group consisting of G148C, T149C, and F150C, and wherein the thiol derivative of plasminogen comprises an amino acid sequence selected from SEQ ID NOs: 13-15.

4. The fibrinolytic composition of claim 1, wherein the catalytic domain comprises the sequence AG, wherein the substitution is selected from the group consisting of A189C and G190C, and wherein the thiol derivative of plasminogen comprises an amino acid sequence selected from SEQ ID NOs: 16-17.

5. The fibrinolytic composition of claim 1, wherein the catalytic domain comprises the sequence FGM, wherein the substitution is selected from the group consisting of F41C, G42C, and M43C, and wherein the thiol derivative of plasminogen comprises an amino acid sequence selected from SEQ ID NOS: 18-20.

6. The fibrinolytic composition of claim 1, wherein the catalytic domain comprises the sequence EKS, wherein the substitution is selected from the group consisting of E64C, K65C, and S66C, and wherein the modified thiol derivative of plasminogen comprises an amino acid sequence selected from SEQ ID NOs: 21-23.

7. The fibrinolytic composition of claim 1, wherein covalently-bound PEG moiety comprises a thiol-reactive, linear or branched polymer having a molecular size from 5 kDa to 40 kDa.

8. A plasminogen variant polypeptide, comprising a substitution of one to eight amino acid residues in a catalytic domain of SEQ ID NO: 2 with a cysteine residue, wherein the plasminogen variant polypeptide comprises an amino acid sequence selected from SEQ ID NOs: 3-23, and a polyethylene glycol (PEG) moiety covalently-bound to the cysteine residue.

9. The plasminogen variant polypeptide of claim 8, consisting of at least 2, 3, and 8 consecutive or alternate or random substitution of amino acid residues with cysteine.

10. The plasminogen variant polypeptide of claim 9, further comprising covalently modified thiol groups at one or more substituted cysteine residues.

11. The plasminogen variant polypeptide of claim 8, wherein the polyethylene glycol moiety is a linear or a branched polymer of varying molecular size ranging from about 5 kDa to about 40 kDa.

12. The plasminogen variant polypeptide of claim 8, wherein the polypeptide is insensitive to alpha2-antiplasmin mediated inhibition.

* * * * *

SEQUENCE LISTING

```
<160> NUMBER OF SEQ ID NOS: 43

<210> SEQ ID NO 1
<211> LENGTH: 791
<212> TYPE: PRT
<213> ORGANISM: Homo sapiens
<220> FEATURE:
<221> NAME/KEY: MISC_FEATURE
<223> OTHER INFORMATION: Native Human Plasminogen

<400> SEQUENCE: 1

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
```

```
                260                 265                 270
Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
            290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
            370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
                420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
            450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
                500                 505                 510

Arg Asn Pro Asp Gly Asp Val Gly Gly Pro Trp Cys Tyr Thr Thr Asn
            515                 520                 525

Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
            595                 600                 605

Pro Arg Pro Ser Ser Tyr Lys Val Ile Leu Gly Ala His Gln Glu Val
            610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
                660                 665                 670

Val Val Ala Asp Arg Thr Glu Cys Phe Ile Thr Gly Trp Gly Glu Thr
            675                 680                 685
```

```
Gln Gly Thr Phe Gly Ala Gly Leu Leu Lys Glu Ala Gln Leu Pro Val
        690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790

<210> SEQ ID NO 2
<211> LENGTH: 249
<212> TYPE: PRT
<213> ORGANISM: Homo sapiens
<220> FEATURE:
<221> NAME/KEY: MISC_FEATURE
<222> LOCATION: (543)..(791)
<223> OTHER INFORMATION: Derivative of  Human Plasminogen/Catalytic
      Domain Microplasminogen (543-791)

<400> SEQUENCE: 2

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240
```

```
Trp Ile Glu Gly Val Met Arg Asn Asn
                245

<210> SEQ ID NO 3
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID No. 2, wherein Glutamic acid at 81 is
      replaced by cysteine

<400> SEQUENCE: 3

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Cys Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 4
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
``` mutant made on SEQ ID NO. 2, wherein Valine at 82 is replaced by cysteine

<400> SEQUENCE: 4

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Cys Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
            165                 170                 175

Arg Val Gln Ser Thr Glu Leu Cys Ala Gly His Leu Ala Gly Gly Thr
        180                 185                 190

Asp Ser Cys Gln Gly Asp Ser Gly Gly Pro Leu Val Cys Phe Glu Lys
    195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
            245

<210> SEQ ID NO 5
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Asparagine at 83 is replaced
      by cysteine

<400> SEQUENCE: 5

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu

-continued

```
                     50                  55                  60
Lys Ser Pro Arg Pro Ser Ser Tyr Lys Val Ile Leu Gly Ala His Gln
 65                  70                  75                  80

Glu Val Cys Leu Glu Pro His Val Gln Glu Ile Glu Val Ser Arg Leu
                     85                  90                  95

Phe Leu Glu Pro Thr Arg Lys Asp Ile Ala Leu Leu Lys Leu Ser Ser
                    100                 105                 110

Pro Ala Val Ile Thr Asp Lys Val Ile Pro Ala Cys Leu Pro Ser Pro
                115                 120                 125

Asn Tyr Val Val Ala Asp Arg Thr Glu Cys Phe Ile Thr Gly Trp Gly
            130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
                180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 6
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Leucine at 84 is replaced by
      cysteine

<400> SEQUENCE: 6

```
Ala Pro Ser Phe Asp Cys Gly Lys Pro Gln Val Glu Pro Lys Lys Cys
 1               5                  10                  15

Pro Gly Arg Val Val Gly Gly Cys Val Ala His Pro His Ser Trp Pro
                 20                  25                  30

Trp Gln Val Ser Leu Arg Thr Arg Phe Gly Met His Phe Cys Gly Gly
                 35                  40                  45

Thr Leu Ile Ser Pro Glu Trp Val Leu Thr Ala Ala His Cys Leu Glu
 50                  55                  60

Lys Ser Pro Arg Pro Ser Ser Tyr Lys Val Ile Leu Gly Ala His Gln
 65                  70                  75                  80

Glu Val Asn Cys Glu Pro His Val Gln Glu Ile Glu Val Ser Arg Leu
                     85                  90                  95

Phe Leu Glu Pro Thr Arg Lys Asp Ile Ala Leu Leu Lys Leu Ser Ser
                    100                 105                 110

Pro Ala Val Ile Thr Asp Lys Val Ile Pro Ala Cys Leu Pro Ser Pro
                115                 120                 125

Asn Tyr Val Val Ala Asp Arg Thr Glu Cys Phe Ile Thr Gly Trp Gly
```

```
            130                 135                 140
Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 7
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Glutamic acid at 85 is
      replaced by cysteine

<400> SEQUENCE: 7

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Cys Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
```

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 8
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Proline at 86 is replaced by
      cysteine

<400> SEQUENCE: 8

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Cys His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 9
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution mutant made on SEQ ID NO. 2, wherein Histidine at 87 is replaced by cysteine

<400> SEQUENCE: 9

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro Cys Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 10
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution mutant made on SEQ ID NO. 2, wherein Valine at 88 is replaced by cysteine

<400> SEQUENCE: 10

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30
```

```
Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
 50                  55                  60

Lys Ser Pro Arg Pro Ser Ser Tyr Lys Val Ile Leu Gly Ala His Gln
 65                  70                  75                  80

Glu Val Asn Leu Glu Pro His Cys Gln Glu Ile Glu Val Ser Arg Leu
                 85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
            210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 11
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution mutant made on SEQ ID NO. 2, wherein Glutamic acid at 85 and Histidine at 87 is replaced by cysteine

<400> SEQUENCE: 11

```
Ala Pro Ser Phe Asp Cys Gly Lys Pro Gln Val Glu Pro Lys Lys Cys
 1               5                  10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
 50                  55                  60

Lys Ser Pro Arg Pro Ser Ser Tyr Lys Val Ile Leu Gly Ala His Gln
 65                  70                  75                  80

Glu Val Asn Leu Cys Pro Cys Val Gln Glu Ile Glu Val Ser Arg Leu
                 85                  90                  95

Phe Leu Glu Pro Thr Arg Lys Asp Ile Ala Leu Leu Lys Leu Ser Ser
            100                 105                 110
```

```
Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
        130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
            165                 170                 175

Arg Val Gln Ser Thr Glu Leu Cys Ala Gly His Leu Ala Gly Gly Thr
        180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
        210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 12
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Valine at 82 and Histidine 87
      is replaced by cysteine

<400> SEQUENCE: 12

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Cys Asn Leu Glu Pro Cys Val Gln Glu Ile Glu Val Ser Arg Leu
            85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
        130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
            165                 170                 175

Arg Val Gln Ser Thr Glu Leu Cys Ala Gly His Leu Ala Gly Gly Thr
        180                 185                 190
```

Asp Ser Cys Gln Gly Asp Ser Gly Pro Leu Val Cys Phe Glu Lys
        195                 200                 205

Asp Lys Tyr Ile Leu Gln Gly Val Thr Ser Trp Gly Leu Gly Cys Ala
210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Glycine at 148 is replaced by
      cysteine

<400> SEQUENCE: 13

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Cys Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 14
<211> LENGTH: 249

```
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Threonine at 149 is replaced
      by cysteine

<400> SEQUENCE: 14
```

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Cys Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

```
<210> SEQ ID NO 15
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Phenylalanine at 150 is
      replaced by cysteine

<400> SEQUENCE: 15
```

Ala Pro Ser Phe Asp Cys Gly Lys Pro Gln Val Glu Pro Lys Lys Cys
1               5                   10                  15

```
Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Cys Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 16
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution mutant made on SEQ ID NO. 2, wherein Alanine at 189 is replaced by cysteine

<400> SEQUENCE: 16

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95
```

```
Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
            130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
            165                 170                 175

Arg Val Gln Ser Thr Glu Leu Cys Ala Gly His Leu Cys Gly Gly Thr
            180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
            210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
            245

<210> SEQ ID NO 17
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Glycine at 190 is replaced by
      cysteine

<400> SEQUENCE: 17

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
            85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
            130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
            165                 170                 175
```

```
Arg Val Gln Ser Thr Glu Leu Cys Ala Gly His Leu Ala Cys Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 18
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Phenylalanine at 41 is
      replaced by cysteine

<400> SEQUENCE: 18

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Cys Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 19
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution mutant made on SEQ ID NO. 2, wherein Glycine at 42 is replaced by cysteine

<400> SEQUENCE: 19

```
Ala Pro Ser Phe Asp Cys Gly Lys Pro Gln Val Glu Pro Lys Lys Cys
1               5                   10                  15
Pro Gly Arg Val Val Gly Gly Cys Val Ala His Pro His Ser Trp Pro
            20                  25                  30
Trp Gln Val Ser Leu Arg Thr Arg Phe Cys Met His Phe Cys Gly Gly
        35                  40                  45
Thr Leu Ile Ser Pro Glu Trp Val Leu Thr Ala Ala His Cys Leu Glu
    50                  55                  60
Lys Ser Pro Arg Pro Ser Ser Tyr Lys Val Ile Leu Gly Ala His Gln
65                  70                  75                  80
Glu Val Asn Leu Glu Pro His Val Gln Glu Ile Glu Val Ser Arg Leu
                85                  90                  95
Phe Leu Glu Pro Thr Arg Lys Asp Ile Ala Leu Leu Lys Leu Ser Ser
            100                 105                 110
Pro Ala Val Ile Thr Asp Lys Val Ile Pro Ala Cys Leu Pro Ser Pro
        115                 120                 125
Asn Tyr Val Val Ala Asp Arg Thr Glu Cys Phe Ile Thr Gly Trp Gly
    130                 135                 140
Glu Thr Gln Gly Thr Phe Gly Ala Gly Leu Leu Lys Glu Ala Gln Leu
145                 150                 155                 160
Pro Val Ile Glu Asn Lys Val Cys Asn Arg Tyr Glu Phe Leu Asn Gly
                165                 170                 175
Arg Val Gln Ser Thr Glu Leu Cys Ala Gly His Leu Ala Gly Gly Thr
            180                 185                 190
Asp Ser Cys Gln Gly Asp Ser Gly Gly Pro Leu Val Cys Phe Glu Lys
        195                 200                 205
Asp Lys Tyr Ile Leu Gln Gly Val Thr Ser Trp Gly Leu Gly Cys Ala
    210                 215                 220
Arg Pro Asn Lys Pro Gly Val Tyr Val Arg Val Ser Arg Phe Val Thr
225                 230                 235                 240
Trp Ile Glu Gly Val Met Arg Asn Asn
                245
```

<210> SEQ ID NO 20
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution mutant made on SEQ ID NO. 2, wherein Methionine at 43 is replaced by cysteine

<400> SEQUENCE: 20

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Cys His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 21
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution mutant made on SEQ ID NO. 2, wherein Glutamic acid at 64 is replaced by cysteine

<400> SEQUENCE: 21

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Cys
    50                  55                  60

Lys Ser Pro Arg Pro Ser Ser Tyr Lys Val Ile Leu Gly Ala His Gln
```

```
                 65                  70                  75                  80
Glu Val Asn Leu Glu Pro His Val Gln Glu Ile Glu Val Ser Arg Leu
                 85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
            115                 120                 125

Asn Tyr Val Val Ala Asp Arg Thr Glu Cys Phe Ile Thr Gly Trp Gly
        130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 22
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Lysine at 65 is replaced by
      cysteine

<400> SEQUENCE: 22

Ala Pro Ser Phe Asp Cys Gly Lys Pro Gln Val Glu Pro Lys Lys Cys
1               5                  10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Cys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
```

```
            145                 150                 155                 160
Pro Val Ile Glu Asn Lys Val Cys Asn Arg Tyr Glu Phe Leu Asn Gly
                    165                 170                 175

Arg Val Gln Ser Thr Glu Leu Cys Ala Gly His Leu Ala Gly Gly Thr
                180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
        210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                    245

<210> SEQ ID NO 23
<211> LENGTH: 249
<212> TYPE: PRT
<213> ORGANISM: Artificial sequence
<220> FEATURE:
<223> OTHER INFORMATION: Mutant
<220> FEATURE:
<221> NAME/KEY: MISC_FEATURE
<222> LOCATION: (543)..(791)
<223> OTHER INFORMATION: Microplasminogen single cysteine substitution
      mutant made on SEQ ID NO. 2, wherein Serine at 66 is replaced by
      cysteine

<400> SEQUENCE: 23

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Cys Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                    165                 170                 175

Arg Val Gln Ser Thr Glu Leu Cys Ala Gly His Leu Ala Gly Gly Thr
                180                 185                 190

Asp Ser Cys Gln Gly Asp Ser Gly Gly Pro Leu Val Cys Phe Glu Lys
            195                 200                 205

Asp Lys Tyr Ile Leu Gln Gly Val Thr Ser Trp Gly Leu Gly Cys Ala
        210                 215                 220

Arg Pro Asn Lys Pro Gly Val Tyr Val Arg Val Ser Arg Phe Val Thr
```

```
                225                 230                 235                 240
Trp Ile Glu Gly Val Met Arg Asn Asn
            245
```

<210> SEQ ID NO 24
<211> LENGTH: 27
<212> TYPE: DNA
<213> ORGANISM: Artificial Sequence
<220> FEATURE:
<223> OTHER INFORMATION: E81C Catalytic Domain forward primer

<400> SEQUENCE: 24
ggtgcgcatc aatgtgttaa tctcgaa                                        27

<210> SEQ ID NO 25
<211> LENGTH: 27
<212> TYPE: DNA
<213> ORGANISM: Artificial Sequence
<220> FEATURE:
<223> OTHER INFORMATION: E81C Catalytic Domain reverse primer

<400> SEQUENCE: 25
ttcgagatta acacattgat gcgcacc                                        27

<210> SEQ ID NO 26
<211> LENGTH: 26
<212> TYPE: DNA
<213> ORGANISM: Artificial Sequence
<220> FEATURE:
<223> OTHER INFORMATION: V82C Catalytic Domain forward primer

<400> SEQUENCE: 26
cacaccagga atgcaatctc gaaccg                                         26

<210> SEQ ID NO 27
<211> LENGTH: 26
<212> TYPE: DNA
<213> ORGANISM: Artificial Sequence
<220> FEATURE:
<223> OTHER INFORMATION: V82C Catalytic Domain reverse primer

<400> SEQUENCE: 27
cggttcgaga ttgcattcct ggtgtg                                         26

<210> SEQ ID NO 28
<211> LENGTH: 26
<212> TYPE: DNA
<213> ORGANISM: Artificial Sequence
<220> FEATURE:
<223> OTHER INFORMATION: N83C Catalytic Domain forward primer

<400> SEQUENCE: 28
accaggaagt gtgtctcgaa ccgcat                                         26

<210> SEQ ID NO 29
<211> LENGTH: 26
<212> TYPE: DNA
<213> ORGANISM: Artificial Sequence
<220> FEATURE:
<223> OTHER INFORMATION: N83C Catalytic Domain reverse primer

<400> SEQUENCE: 29
atgcggttcg agacacactt cctggt                                         26

<210> SEQ ID NO 30

```
<211> LENGTH: 29
<212> TYPE: DNA
<213> ORGANISM: Artificial Sequence
<220> FEATURE:
<223> OTHER INFORMATION: L84C Catalytic Domain forward primer

<400> SEQUENCE: 30
aagaagtgaa ttgtgaaccg catgtccag                                29

<210> SEQ ID NO 31
<211> LENGTH: 29
<212> TYPE: DNA
<213> ORGANISM: Artificial Sequence
<220> FEATURE:
<223> OTHER INFORMATION: L84C Catalytic Domain reverse primer

<400> SEQUENCE: 31
ctggacatgc ggttcacaat tcacttctt                                29

<210> SEQ ID NO 32
<211> LENGTH: 22
<212> TYPE: DNA
<213> ORGANISM: Artificial Sequence
<220> FEATURE:
<223> OTHER INFORMATION: E85C Catalytic Domain forward primer

<400> SEQUENCE: 32
agtgaatctt tgtccgcatg tt                                       22

<210> SEQ ID NO 33
<211> LENGTH: 22
<212> TYPE: DNA
<213> ORGANISM: Artificial Sequence
<220> FEATURE:
<223> OTHER INFORMATION: E85C Catalytic Domain reverse primer

<400> SEQUENCE: 33
aacatgcgga caaagattca ct                                       22

<210> SEQ ID NO 34
<211> LENGTH: 21
<212> TYPE: DNA
<213> ORGANISM: Artificial Sequence
<220> FEATURE:
<223> OTHER INFORMATION: P86C Catalytic Domain forward primer

<400> SEQUENCE: 34
aatctcgaat gtcatgtcca g                                        21

<210> SEQ ID NO 35
<211> LENGTH: 21
<212> TYPE: DNA
<213> ORGANISM: Artificial Sequence
<220> FEATURE:
<223> OTHER INFORMATION: P86C Catalytic Domain reverse primer

<400> SEQUENCE: 35
ctggacatga cattcgagat t                                        21

<210> SEQ ID NO 36
<211> LENGTH: 24
<212> TYPE: DNA
<213> ORGANISM: Artificial Sequence
<220> FEATURE:
<223> OTHER INFORMATION: H87C Catalytic Domain forward primer

<400> SEQUENCE: 36
```
aatctagaac cgtgtgtgca ggaa                                           24

<210> SEQ ID NO 37
<211> LENGTH: 24
<212> TYPE: DNA
<213> ORGANISM: Artificial Sequence
<220> FEATURE:
<223> OTHER INFORMATION: H87C Catalytic Domain reverse primer

<400> SEQUENCE: 37
ttcctgcaca cacggttcta gatt                                           24

<210> SEQ ID NO 38
<211> LENGTH: 25
<212> TYPE: DNA
<213> ORGANISM: Artificial Sequence
<220> FEATURE:
<223> OTHER INFORMATION: V88C Catalytic Domain forward primer

<400> SEQUENCE: 38
cgaaccgcat tgtcaggaga tagaa                                          25

<210> SEQ ID NO 39
<211> LENGTH: 25
<212> TYPE: DNA
<213> ORGANISM: Artificial Sequence
<220> FEATURE:
<223> OTHER INFORMATION: V88C Catalytic Domain reverse primer

<400> SEQUENCE: 39
ttctatctcc tgacaatgcg gttcg                                          25

<210> SEQ ID NO 40
<211> LENGTH: 21
<212> TYPE: DNA
<213> ORGANISM: Artificial Sequence
<220> FEATURE:
<223> OTHER INFORMATION: F41C Catalytic Domain forward primer

<400> SEQUENCE: 40
agaactaggt gtggaatgca t                                              21

<210> SEQ ID NO 41
<211> LENGTH: 21
<212> TYPE: DNA
<213> ORGANISM: Artificial Sequence
<220> FEATURE:
<223> OTHER INFORMATION: F41C Catalytic Domain reverse primer

<400> SEQUENCE: 41
atgcattcca cacctagttc t                                              21

<210> SEQ ID NO 42
<211> LENGTH: 21
<212> TYPE: DNA
<213> ORGANISM: Artificial Sequence
<220> FEATURE:
<223> OTHER INFORMATION: M43C Catalytic Domain forward primer

<400> SEQUENCE: 42
aggtttggat gtcacttctg t                                              21

<210> SEQ ID NO 43
<211> LENGTH: 21
<212> TYPE: DNA

```
<213> ORGANISM: Artificial Sequence
<220> FEATURE:
<223> OTHER INFORMATION: M43C Catalytic Domain reverse primer

<400> SEQUENCE: 43
acagaagtga catccaaacc t                                              21
```